(12) United States Patent
Kleinschnitz et al.

(10) Patent No.: US 9,452,203 B2
(45) Date of Patent: Sep. 27, 2016

(54) USE OF C1-INHIBITOR FOR THE TREATMENT OF SECONDARY EDEMA OF THE CENTRAL NERVOUS SYSTEM

(71) Applicant: CSL BEHRING GMBH, Marburg (DE)

(72) Inventors: Christoph Kleinschnitz, Hettstadt (DE); Marc Nolte, Michelbach (DE); Guido Stoll, Rimpar (DE); Gerhard Dickneite, Marburg (DE); Stefan Schulte, Marburg (DE); Bernhard Nieswandt, Eibelstadt (DE); Ingo Pragst, Edertal (DE)

(73) Assignee: CSL BEHRING GMBH, Marburg (DE)

( * ) Notice: Subject to any disclaimer, the term of this patent is extended or adjusted under 35 U.S.C. 154(b) by 0 days.

(21) Appl. No.: 14/364,097

(22) PCT Filed: Dec. 21, 2012

(86) PCT No.: PCT/EP2012/076691
§ 371 (c)(1),
(2) Date: Jun. 10, 2014

(87) PCT Pub. No.: WO2013/093027
PCT Pub. Date: Jun. 27, 2013

(65) Prior Publication Data
US 2014/0371425 A1    Dec. 18, 2014

Related U.S. Application Data

(60) Provisional application No. 61/587,371, filed on Jan. 17, 2012.

(30) Foreign Application Priority Data

Dec. 22, 2011 (EP) .................................. 11195254

(51) Int. Cl.
*A61K 38/17* (2006.01)
*A61K 38/57* (2006.01)

(52) U.S. Cl.
CPC ..................... *A61K 38/57* (2013.01)

(58) Field of Classification Search
None
See application file for complete search history.

(56) References Cited

U.S. PATENT DOCUMENTS 4,915,945 A   4/1990  Pelzer et al.
5,939,389 A   8/1999  Eisele et al.
6,284,365 B1  9/2001  Hirose et al.
7,053,176 B1  5/2006  Häfner et al.

FOREIGN PATENT DOCUMENTS

WO   WO 01/79271 A1    10/2001
WO   WO 2007/073186 A2  6/2007

OTHER PUBLICATIONS

Akita et al., "Protective Effect of C1 Esterase Inhibitor on Reperfusion Injury in the Rat Middle Cerebral Artery Occlusion Model", Neurosurgery, vol. 52, No. 2, Feb. 2003, pp. 395-401.
Austinat et al., "Blockade of Bradykinin Receptor B1 but not Bradykinin Receptor B2 Provides Protection from Cerebral Infarction and Brain Edema", Stroke, vol. 40, Jan. 2009, pp. 285-293.
Ayata et al., "Ischaemic brain oedema", Journal of Clinical Neuroscience, vol. 9, No. 2, 2002, pp. 113-124.
Bardutzky et al., "Antiedema Therapy in Ischemic Stroke", Stroke, vol. 38, 2007, pp. 3084-3094.
Barone et al., "Endothelin Levels Increase in Rat Focal and Global lschemia", Journal of Cerebral Blood Flow and Metabolism, vol. 14, No. 2, 1994, pp. 337-342.
Bederson et al., "Evaluation of 2,3,5-Triphenyltetrazolium Chloride as a Stain for Detection and Quantification of Experimental Cerebral Infarction in Rats", Stroke, vol. 17, No. 6, 1986, pp. 1304-1308.
Bederson et al., "Rat Middle Cerebral Artery Occlusion: Evaluation of the Model and Development of a Neurologic Examination", Stroke, vol. 17, No. 3, 1986, pp. 472-476.
Beynon et al., "Schweres Schädel-Hirn-Trauma", Unfallchirurg, vol. 114, No. 8, 2011, pp. 713-723.
Cai et al., "Complement Regulatory Protein C1 Inhibitor Binds to Selectins and Interferes with Endothelial-Leukocyte Adhesion", The Journal of Immunology, vol. 171, 2003, pp. 4786-4791.
Davis III et al., "Biological activities of C1 Inhibitor", Molecular Immunology, vol. 45, 2008 (available online Jul. 31, 2008), pp. 4057-4063.

(Continued)

*Primary Examiner* — John Ulm
(74) *Attorney, Agent, or Firm* — Birch, Stewart, Kolasch & Birch, LLP

(57) ABSTRACT

The subject of the present invention is, in the most general aspect, the prevention and/or treatment of a secondary edema. In particular, the present invention relates to a C1-Inhibitor for use in a method of preventing the formation and/or reducing the size of a secondary edema of the central nervous system (CNS) in a subject wherein the subject has or has had at least one disorder selected from the group consisting of stroke, ischemic stroke, hemorrhagic stroke, perinatal stroke, traumatic brain injury and spinal cord injury. Preferably the secondary edema of the CNS is a secondary brain edema. Another subject of the present invention is the treatment of disorders associated with an increased permeability of the blood brain barrier or the blood spinal cord barrier. And a third subject is a plasma-derived C1-inhibitor for use in a method of preventing, reducing or treating brain ischemia-reperfusion injury.

30 Claims, 12 Drawing Sheets

(5 of 12 Drawing Sheet(s) Filed in Color)

(56) References Cited

OTHER PUBLICATIONS

De Simoni et al., "The Powerful Neuroprotective Action of C1-Inhibitor on Brain Ischemia-Reperfusion Injury Does Not Require C1q", American Journal of Pathology, vol. 164, No. 5, May 2004, pp. 1857-1863.

Ducruet et al., "The complement cascade as a therapeutic target in intracerebral hemorrhage", Experimental Neurology, vol. 219, 2009 (available online Jul. 24, 2009), pp. 398-403.

European Search Report, dated Jun. 8, 2012, for European Application No. 11195254.5.

Friesecke et al., "C1-Esterase-Inhibitor als Ultima-ratio-Therapie bei volumen—und katecholaminrefraktärem Schock infolge Ischämie-Reperfusionsschaden nach langer Reanimation", Intensivmed, vol. 39, 2002, XP-002378004, pp. 610-616.

Gesuete et al., "Recombinant C1 Inhibitor in Brain Ischemic Injury", Ann Neurol, vol. 66, 2009, XP-002676459, pp. 332-342.

Hagedorn et al., "Factor XIIa Inhibitor Recombinant Human Albumin Infestin-4 Abolishes Occlusive Arterial Thrombus Formation Without Affecting Bleeding", Circulation, vol. 121, 2010 (published online Mar. 22, 2010), pp. 1510-1517.

International Search Report and Written Opinion of the International Searching Authority, dated Feb. 12, 2013, for International Application No. PCT/EP2012/076691.

Kleinschnitz et al., "Glucocorticoid Insensitivity at the Hypoxic Blood-Brain Barrier Can Be Reversed by Inhibition of the Proteasome", Stroke, vol. 42, 2011 (published online Feb. 17, 2011), pp. 1081-1089.

Kleinschnitz et al., "Post-Stroke Inhibition of Induced NADPH Oxidase Type 4 Prevents Oxidative Stress and Neurodegeneration", PLoS Biology, vol. 8, Issue 9, Sep. 2010, pp. 1-13.

Kleinschnitz et al., "Targeting coagulation factor XII provides protection from pathological thrombosis in cerebral ischemia without interfering with hemostasis", The Journal of Experimental Medicine, vol. 203, No. 3, Mar. 20, 2006, pp. 513-518.

Kraft et al., "Thrombin-Activatable Fibrinolysis Inhibitor (TAFI) Deficient Mice Are Susceptible to Intracerebral Thrombosis and Ischemic Stroke", PLOS ONE, vol. 5, Issue 7, Jul. 2010, pp. 1-6.

Leeb-Lundberg et al., "International Union of Pharmacology. XLV. Classification of the Kinin Receptor Family: from Molecular Mechanisms to Pathophysiological Consequences", Pharmacological Reviews, vol. 57, No. 1, 2005, pp. 27-77.

Livak et al., "Analysis of Relative Gene Expression Data Using Real-Time Quantitative PCR and the $2^{-\Delta\Delta CT}$ Method", Methods, vol. 25, 2001, pp. 402-408.

Longa et al., "Reversible Middle Cerebral Artery Occlusion Without Craniectomy in Rats", Stroke, vol. 20, 1989, pp. 84-91.

Longhi et al., C1-inhibitor attenuates neurobehavioral deficits and reduces contusion volume after controlled cortical impact brain injury in mice, Crit Care Med, vol. 37, No. 2, 2009, pp. 659-665.

Matsuo et al., "Protective Effect of Endothelin Type A Receptor Antagonist on Brain Edema and Injury After Transient Middle Cerebral Artery Occulusion in Rats", Stroke, vol. 32, 2001, pp. 2143-2148.

Moran et al., "Age-related learning deficits in transgenic mice expressing the 751-amino acid isoform of human β-amyloid precursor protein", Proc. Natl. Acad. Sci. USA, vol. 92, Jun. 1995, pp. 5341-5345.

Nag et al., "Pathology and new players in the pathogenesis of brain edema", Acta Neuropathol, vol. 118, 2009 (published online Apr. 30, 2009), pp. 197-217.

Raslan et al., "Inhibition of bradykinin receptor B1 protects mice from focal brain injury by reducing blood-brain barrier leakage and inflammation", Journal of Cerebral Blood Flow & Metabolism, vol. 30, 2010 (published online Mar. 3, 2010), pp. 1477-1486.

Sangha et al., "Treatment Targets in Intracerebral Hemorrhage", Neurotherapeutics, vol. 8, 2011, pp. 374-387.

Storini et al., "C1-inhibitor protects against brain ischemia-reperfusion injury via inhibition of cell recruitment and inflammation", Neurobiology of Disease, vol. 19, 2005 (Available online Feb. 21, 2005), pp. 10-17.

Tei et al., "Protective effect of C1 esterase inhibitor on acute traumatic spinal cord injury in the rat", Neurological Research, Sep. 2008, vol. 30, pp. 761-767.

Thornton et al., "Kinin Receptor Antagonists as Potential Neuroprotective Agents in Central Nervous System Injury", Molecules, vol. 15, 2010, pp. 6598-6618.

Wagner et al., "Activation of the tissue kallikrein-kinin system in stroke", Journal of the Neurological Sciences, vol. 202, 2002, pp. 75-76.

Patent Examination Report issued Aug. 5, 2014, in Australian Patent Application No. 2012318275.

International Preliminary Report on Patentability and Written Opinion issued Jul. 3, 2014, in PCT International Application No. PCT/EP2012/076691.

USE OF C1-INHIBITOR FOR THE TREATMENT OF SECONDARY EDEMA OF THE CENTRAL NERVOUS SYSTEM

CROSS-REFERENCE TO RELATED APPLICATIONS

The present application is the national stage entry of PCT/EP2012/076691 filed on Dec. 21, 2012. The present application claims priority to provisional application 61/587,371 filed on Jan. 17, 2012.

STATEMENT REGARDING FEDERAL SPONSORED RESEARCH AND DEVELOPMENT

Not applicable.

BACKGROUND OF THE INVENTION

The subject of the present invention is, in the most general aspect, the prevention and/or treatment of a secondary edema. In particular, the present invention relates to a C1-Inhibitor for use in a method of preventing the formation and/or reducing the size of a secondary edema of the central nervous system (CNS) in a subject wherein the subject has or has had at least one disorder selected from the group consisting of stroke, ischemic stroke, hemorrhagic stroke, perinatal stroke, traumatic brain injury and spinal cord injury. Preferably the secondary edema of the CNS is a secondary brain edema. Another subject of the present invention is the treatment of disorders associated with an increased permeability of the blood brain barrier or the blood spinal cord barrier. And a third subject is a plasma-derived C1-inhibitor for use in a method of preventing, reducing or treating brain ischemia-reperfusion injury.

In this specification, a number of documents are cited. The disclosure content of these documents including manufacturer's manuals is herewith incorporated by reference in its entirety.

The pathology of brain ischemia and the subsequent injury due to reperfusion (brain ischemia-reperfusion injury) is complex and involves a myriad of distinct molecular and cellular pathways. Among these one characteristic of persisting ischemia is structural disintegration of the blood-brain-barrier which in consequence leads to the formation of brain edema. Excessive edema can harm otherwise healthy brain regions simply by mechanic compression and is a frequent cause of worsening of neurological symptoms in stroke patients. Up to now convincing strategies on a pharmacological basis to combat edema formation in acute ischemic stroke are lacking.

Brain edema is defined as an increase in brain volume resulting from a localized or diffuse abnormal accumulation of fluid within the brain parenchyma. In general, brain edema is classified into 4 different groups: vasogenic, cytotoxic, hydrocephalic (or interstitial) and osmotic (or hypostatic) edema. Despite this classification of distinct forms of edema, in most clinical situations there is a combination of different types of edema depending on the time course of the disease. Regarding edema formation subsequent to disturbed cerebral blood flow and cerebral bleeding the cytotoxic and/or vasogenic brain edema seem to play major roles. Moreover, looking at the mediators involved in brain edema formation, many mediators can be mentioned (e.g. Bradykinin), which have many properties other than their effects on brain edema formation (Nag et al. (2009) *Acta Neuropathol.;* 118:197-217).

Initially in brain edema, the changes in brain volume are compensated by a decrease in cerebrospinal fluid and blood volume, whereby the primary brain edema is mainly a cytotoxic edema. In large hemispheric lesions, progressive swelling exceeds these compensatory mechanisms and an increase in the intracranial pressure (i.e. formation of secondary or malignant brain edema) results in herniations of cerebral tissue leading to death. Hence vasogenic, malignant brain edema continues to be a major cause of mortality after diverse types of brain pathologies such as major cerebral infarcts, hemorrhages, trauma, infections and tumors. The lack of effective treatment for brain edema remains a stimulus for continued interest and research.

Regarding ischemic stroke, secondary brain edema is a frequent cause of secondary infarct growth and subsequent deterioration of neurological symptoms during the course of ischemic stroke (Ayata and Ropper (2002) *J Clin Neurosci.;* 9:113-124; Bardutzky and Schwab (2007) *Stroke;* 38:3084-3094). In ischemic stroke malignant middle cerebral artery (MCA) infarction is a term used to describe complete MCA territory infarction with significant space occupying effect and herniation of brain tissue. The incidence of malignant MCA infarction is estimated to be less than 1% of all strokes. The mortality with conservative forms of medical treatment is approximately 80% and coma terminates in brain death within 2-5 days of onset. Death usually occurs from progressive swelling of the ischemic brain tissue, brain tissue shifts, focal increase in intracranial pressure, and the extension of ischemia to adjacent vascular territories. Survivors of this kind of stroke are disabled with poor quality of life. So far no medication has proven to persistently reduce brain edema in cerebral ischemia and often the last treatment approach as life saving procedure is the decompressive hemicraniectomy. Furthermore, molecular mechanisms underlying edema formation and successive neuronal degeneration in ischemic stroke are largely unknown.

The kallikrein-kinin system (KKS) is initiated by blood coagulation factor XII (FXII, Hageman factor) and plays an important role in the regulation of vascular permeability and edema formation (Leeb-Lundberg et al. (2005) *Pharmacol. Rev.;* 571:27-77). The activation of the KKS was recently proven also in stroke patients (Wagner et al. (2002) *J. Neurol. Sci.;* 202:75-76). Kinins (e.g. bradykinin, kallidin) constitute the end products of the KKS. Kinins are highly active proinflammatory peptide hormones which are released by kallikreins from their precursors, kininogens, during various kinds of tissue injury including brain ischemia. The cellular effects of kinins are mediated by two different bradykinin receptors, B1R and B2R. Activation of these receptors triggers inflammatory processes in the target organ such as the release of proinflammatory cytokines or the attraction of immune cells as well as increased vascular permeability.

Recently, blockade of B1R, but not B2R, reduced blood-brain-barrier damage and edema formation in experimental models of focal cerebral ischemia (Austinat et al. (2009) *Stroke;* 40:285-293) and traumatic brain injury (Raslan et al. (2010) *J. Cereb. Blood Flow Metab.;* 30:1477-1486) in mice suggesting functional relevance of KKS on brain edema formation in the acute phase of ischemic stroke and traumatic brain injury.

In studies preventing the activation of KKS via inhibition of FXII, which is activated physiologically upon contact with negatively charged surfaces (contact activation), neuropathological outcome following acute experimental stroke (Hagedorn et al. (2010) *Circulation;* 121:1510-1517; Kleinschnitz et al. (2006) *JEM;* 203(3):513). was investigated.

C1-esterase inhibitor (C1-INH) is a 478 amino acid glycoprotein belonging to the superfamily of serine protease inhibitors called serpins. Its designation originates from the initial description as the only known physiological inhibitor of the classical complement pathway in blood and tissue. However, C1-INH is also a major regulator of the KKS by blocking activated FXII and plasma kallikrein. Apart from several other functions (e.g. FXIa inhibition), it is the only known physiological inhibitor of C1s and C1r, the activated homologous serin proteases of the first component of the complement system.

Previous studies have demonstrated a beneficial role of C1-INH formulations in animal models of ischemic stroke itself (De Simoni et al. (2004) *Am. J. Pathol.;* 164:1857-1863; Gesuete et al. (2009) *Ann. Neurol.;* 66:332-342) as well as of traumatic brain injury (Longhi et al. (2009) *Crit. Care Med.;* 37:659-665) and traumatic spinal cord injury (Tei et al. (2008) *Neurol. Res.;* 30:761-767) but the underlying molecular mechanisms are largely unknown. Furthermore, these studies were focussing on acute neuropathological outcomes whereas effects on (secondary) brain edema, i.e. preventing its formation and/or reducing its size, were not disclosed. In addition, de Simoni et al. (2004; *Am. J. Pathol.;* 164:1857-1863) disclose that plasma-derived C1-inhibitor (15 U/mouse) was just effective in the murine model of ischemia/reperfusion injury when given at the start of reperfusion, whilst efficacy was completely lost when given 30 minutes after start of reperfusion.

Hence, it is apparent that there still exists a need for a medication for the treatment or prophylaxis of a secondary brain edema occurring after an occlusion of a blood vessel in the brain. Therefore, it is an object of the present invention to satisfy such a need.

BRIEF SUMMARY OF THE INVENTION

Thus, the technical problem underlying the present invention was to provide alternative and/or improved means and methods for successfully targeting secondary brain edema that form the basis or may allow the development of more satisfactory medicaments for the treatment and/or prevention of the secondary brain edema.

The solution to this technical problem is achieved by providing the embodiments characterized in the claims.

Surprisingly the applicant has discovered that a secondary brain edema occurring subsequent to an initial injury could be prevented or reduced by the administration of C1-inhibitor. Such an initial injury or primary disorder could be an occlusion of a blood vessel in the brain, e.g. an ischemic stroke, or to a hemorrhage in the brain, e.g. a hemorrhagic stroke.

DETAILED DESCRIPTION OF THE INVENTION

Accordingly, in general the present invention relates to a C1-Inhibitor for use in a method of preventing the formation and/or reducing the size of a secondary edema of the central nervous system (CNS) in a subject wherein the subject has or has had at least one disorder selected from the group consisting of stroke, ischemic stroke, hemorrhagic stroke, perinatal stroke, traumatic brain injury, and spinal cord injury. In particular the hemorrhagic stroke is a cerebral hemorrhage or a subarachnoidal hemorrhage.

In a preferred embodiment of the invention the secondary edema of the central nervous system (CNS) is a secondary brain edema or a secondary spinal cord edema.

Another aspect of the present invention is a C1-inhibitor for stabilizing the blood brain barrier or the blood spinal cord barrier in a subject wherein the subject has or has had at least one disorder selected from the group consisting of stroke, ischemic stroke, hemorrhagic stroke, perinatal stroke, traumatic brain injury, spinal cord injury, diabetes mellitus, multiple sclerosis, a bacterial infection of the CNS like meningitis, viral infection infecting the brain like HIV, and brain tumor, in particular metastasing brain tumor is provided.

Therefore, a C1-inhibitor for treating disorders associated with an increased permeability of the blood brain barrier or the blood spinal cord barrier in a subject is claimed, wherein the disorder is selected from the group consisting of stroke, ischemic stroke, hemorrhagic stroke, perinatal stroke, traumatic brain injury, spinal cord injury, diabetes mellitus, multiple sclerosis, a bacterial infection of the CNS like meningitis, viral infection infecting the brain like HIV, and brain tumor, in particular metastasing brain tumor.

In addition, a C1-inhibitor for use in a method of preventing or reducing an increased permeability of the blood brain barrier or the blood spinal cord barrier in a subject is claimed wherein this increased permeability is associated with an disorder is selected from the group consisting of stroke, ischemic stroke, hemorrhagic stroke, perinatal stroke, traumatic brain injury, spinal cord injury, diabetes mellitus, multiple sclerosis, a bacterial infection of the CNS, preferably meningitis, viral infection infecting the brain, preferably HIV, and brain tumor, preferably metastasing brain tumor.

A third aspect of the present invention is a plasma-derived C1-inhibitor for use in a method of preventing, reducing or treating brain ischemia-reperfusion injury in a subject whereby the inhibitor is administered 30 minutes or more after start of reperfusion.

In certain embodiments regarding the treatment of brain ischemia-reperfusion injury with the plasma-derived C1-inhibitor said brain ischemia-reperfusion injury occurs after a disorder selected from the group consisting of stroke, ischemic stroke, hemorrhagic stroke and perinatal stroke.

According to the present invention the terms "C1-Inhibitor," "C1 esterase Inhibitor," and "C1-INH" refer to the proteins or fragments thereof that function as serine protease inhibitors to inhibit proteases associated with the complement system, preferably proteases C1r and C1s as well as MASP-1 and MASP-2, with the kallikrein-kinin system, preferably plasma kallikrein and factor XIIa, and with the coagulation system, preferably factor XIa. In addition, C1-INH can serve as an anti-inflammatory molecule that reduces the selectins-mediated leukocyte adhesion to endothelial cells. C1-INH as used here can be a native serine protease inhibitor or active fragment thereof, or it can comprise a recombinant peptide, a synthetic peptide, peptide mimetic, or peptide fragment that provides similar functional properties—e.g., the inhibition of proteases C1r and C1 s, and/or MASP-1 and MASP-2 and/or factor XIIa and/or factor XIa. For further disclosure regarding the structure and function of C1-Inhibitor, see U.S. Pat. No. 4,915,945; U.S. Pat. No. 5,939,389; U.S. Pat. No. 6,248,365; U.S. Pat. No. 7,053,176; and WO 2007/073186, which are hereby incorporated in their entirety.

Therefore in a preferred embodiment of the present invention the inhibitor is a plasma-derived or a recombinant C1-Inhibitor. In a further preferred embodiment said inhibitor is identical with the naturally occurring human protein or a variant thereof. The C1-INH shall encompass all natural occurring alleles which have the same function as the C1-inhibitor. In the most preferred embodiment said inhibitor is the human C1 Esterase Inhibitor.

In another preferred embodiment the C1-inhibitor according to the present invention is modified to improve bioavailability and/or half-life, to improve efficacy and/or to reduce potential side effects. The modification can be realized by recombinant or other steps. Examples for such a modification could be a glycosylation or an albumin fusion of the described C1-inhibitor. For further disclosure regarding the glycosylation and the albumin fusion of proteins see WO 01/79271, which is hereby incorporated in their entirety.

In various embodiments, C1-Inhibitor can be produced according to methods known to one of skill in the art. For example, plasma-derived C1-INH can be prepared by collecting blood plasma from several donors. Donors of plasma should be healthy as defined in the art. Preferably, the plasma of several (1000 or more) healthy donors is pooled and optionally further processed. An exemplary process for preparing C1-inhibitor for therapeutic purposes is disclosed in U.S. Pat. No. 4,915,945, the disclosure of which is hereby incorporated in its entirety. Alternatively, in some embodiments C1-INH can be collected and concentrated from natural tissue sources using techniques known in the art. Commercially available products comprising C1-inhibitor are, e.g. plasma-derived Cinryze® (Viropharma), recombinant Ruconest® or Rhucin® (both Pharming), and plasma-derived Berinert® (CSL Behring). Berinert® is indicated for treatment of hereditary angioedema and congenital deficiencies. Recombinant C1-INH can be prepared by known methods.

The term "edema of the central nervous system" or "edema of CNS" refers to an excess accumulation of water in the intracellular and/or extracellular spaces of the central nervous system (CNS). The term "cerebral edema" or "brain edema" refers to an excess accumulation of water in the intracellular and/or extracellular spaces of the brain. The pathophysiology even of acute or primary edema of CNS, preferably primary brain edema formation, and in particular the occurrence of temporally-delayed (i.e. hours or days after stroke onset) malignant or secondary edema of CNS, preferably a secondary brain edema, and its involved (molecular) pathomechanisms are largely unknown and seem to be rather complex. Regarding edema formation subsequent to disturbed cerebral blood flow and cerebral bleeding the vasogenic and/or cytotoxic brain edema seem to play major roles.

The primary edema of CNS, preferably the primary brain edema, is an edema occurring during the initial insult or shortly or immediately (i.e. within minutes) after the insult. It is mainly a cytotoxic edema resulting from abnormal water uptake by injured brain cells.

In contrast, the secondary edema of CNS, preferably the secondary brain edema, occurs later, i.e. hours or even days after the insult, and is mainly a vasogenic edema. In e.g. traumatic brain injury (TBI) the malignant cerebral edema is a rare (<10%), but often fatal (~100%) complication. It is diagnosed by a rapid increase in intracranial pressure (ICP) within hours after injury that is refractory to medical management.

Therefore as used herein, the terms "secondary brain edema" or "secondary cerebral edema" or "malignant brain edema" or "malignant cerebral edema" refer to any delayed post-injury brain swelling i.e. the late swelling occurs within hours or days after the initial injury. In particular the secondary brain edema according to the invention is substantially a vasogenic edema. In this type of edema, due to breakdown of the blood brain barrier, normally excluded intravascular proteins and fluid penetrate into cerebral parenchymal extracellular space. Once plasma constituents cross the blood brain barrier, the edema spreads and this may be quite fast and widespread.

And as used herein, the term "secondary spinal cord edema" refers to any delayed post-injury swelling of the spinal cord, i.e. the late swelling occurs within hours or days after the initial injury. In particular the secondary spinal cord edema according to the invention is substantially a vasogenic edema. In this type of edema normally excluded intravascular proteins and fluid penetrate into cerebral parenchymal extracellular space. Once plasma constituents cross the blood spinal cord barrier, the edema spreads and this may be quite fast and widespread.

Preferably the secondary edema occurs 1 to 10 days, more preferably 2 to 5 days after the initial injury leading to the at least one disorder, which is related to the secondary brain edema. In some embodiments the secondary edema appears 2, 3, 4, or 5 days after the initial insult or at any time each between.

The term "preventing the formation of a secondary edema" refers to methods of use of the C1-inhibitor where the formation of a secondary edema is prevented in total or partly. Prevention of the formation of a secondary edema in total means that a secondary edema does not occur at all if the C1-inhibitor is administered in advance of the formation. Preventing the formation of a secondary edema partly means reducing the size of a secondary edema in a scenario where the C1-inhibitor is administered at a time before the secondary edema has started to occur and the size of the later occurring edema will be smaller than the size of an edema in an untreated patient. In a preferred embodiment of the invention the size of the secondary edema, i.e. the volume of the secondary edema, is prevented by at least 10%, 20%, 30%, 40%, 50%, 60%, 70%, 80%, 90% (or by any percentage in between) compared to the size of the untreated secondary edema.

As used here, the term "reducing" comprises lowering the likelihood of a secondary edema in an individual or in an animal, lowering the severity of any symptoms, and/or lowering the proportion of patients in a population at risk for secondary edema following an initial injury. Thus, "reducing" refers to decreasing, lowering, lessening, limiting, ameliorating, or improving a condition of secondary edema. Reducing the size of a secondary edema may include, for example, protecting against the occurrence of a secondary edema; reducing the risk of a secondary edema, reducing the severity of a secondary edema as it develops, or once it has developed; limiting the damage of a secondary edema; reducing the spread of a secondary edema, e.g. limiting the volume of the edema developed after an initial insult; or improving conditions in the brain or the spinal cord associated with a secondary edema.

The term "reducing the size of a secondary edema" refers to methods of use of the C1-inhibitor where the size of a secondary edema is reduced independently whether the formation of the secondary edema has started at the moment of administration or not. Therefore reducing the size of a secondary edema means reducing the volume of a secondary edema in a scenario where the C1-inhibitor is administered to reduce the size of an already existing secondary edema which will occur after the administration as well as in a scenario where the C1-INH is administered to reduce the size of an already occurred, but still growing secondary edema. In a preferred embodiment of the invention reducing the size of a secondary edema means that the size of the secondary edema is reduced by at least 10%, 20%, 30%, 40%, 50%, 60%, 70%, 80%, 90% (or by any percent in between) compared to the size or the volume of the untreated secondary edema, i.e. in absence of therapy.

Therefore, in a preferred embodiment of the invention the size of the secondary edema is reduced by at least 10%, preferably by at least 20%, more preferably by at least 30%, more preferably by at least 40%, more preferably by at least 50%, more preferably by at least 60%, more preferably by at least 70%, more preferably by at least 80%, more preferably by at least 90% compared to the volume of the untreated secondary edema.

In certain embodiments of the invention said treatment of a secondary edema in a subject is prophylactic and/or therapeutic. The use of the C1 inhibitor according to the invention can be used prophylactically and/or therapeutically to prevent the formation of a secondary edema and/or to reduce the size of a secondary edema.

The disorder which is related to the secondary edema is induced by an initial injury, which is used herein alternatively to the term "initial insult", i.e. the initial insult leads to the at least one disorder which is related to the secondary edema. An Example for an initial insult according to the present invention is a brain ischemia. Preferably this initial injury could be an occlusion of a blood vessel, e.g. an ischemic stroke, or a hemorrhage, e.g. a hemorrhagic stroke. More preferably the initial insult is an occlusion of a blood vessel in the brain or a hemorrhage in the brain.

The at least one disorder, which is related to the secondary edema, is selected from the group consisting of stroke, ischemic stroke, hemorrhagic stroke, perinatal stroke, traumatic brain injury, and spinal cord injury. Alternatively the C1-INH can be administered to a subject who has a disorder like an infection or a brain tumor.

The term "stroke" as used in the present invention is well-known in the art and sometimes also referred to as cerebrovascular accident (CVA) or cerebral infarction. A stroke is a medical condition that is medically defined by reduced blood supply to the brain resulting in loss of brain function, inter alia due to ischemia. Said reduction in blood supply can be caused, for example, by thrombosis or embolism. In addition stroke can be caused by haemorrhagic processes. Hence, strokes are generally classified into two major categories, i.e., i) ischemic and ii) hemorrhagic strokes. Ischemia is due to an interruption in blood circulation and hemorrhage is due to a rupture of a blood vessel or an abnormal vascular structure, both scenarios ultimately leading to a damage of brain tissue. About 87% of strokes are caused by ischemia, and the remainder by hemorrhage. Some hemorrhages develop inside areas of ischemia ("hemorrhagic transformation"). It is unknown how many hemorrhages actually start as ischemic stroke.

According to the present invention, said stroke is therefore preferably an ischemic stroke or a hemorrhagic stroke.

In an ischemic stroke, blood supply to part of the brain is decreased, leading to dysfunction and necrosis of the brain tissue in that area. There are mainly three causative reasons: thrombosis (obstruction of a blood vessel by a blood clot forming locally), embolism (idem due to a blood clot/embolus from elsewhere in the body) and systemic hypoperfusion (general decrease in blood supply, e.g. in shock). According to the invention the thrombosis can occur preferably in arteries, veins, arterioles, venules, and capillaries whereas the embolism can occur preferably in arteries, arterioles, and capillaries.

A hemorrhagic stroke, i.e. an intracranial hemorrhage, is the accumulation of blood anywhere within the skull vault. A distinction is made between intra-axial hemorrhage (blood inside the brain) and extra-axial hemorrhage (blood inside the skull but outside the brain).

In a particularly preferred embodiment of the invention, said hemorrhagic stroke is a cerebral hemorrhage or a subarachnoidal hemorrhage.

A cerebral hemorrhage or intracerebral hemorrhage is a subtype of intracranial hemorrhage that occurs within the brain tissue itself. Cerebral hemorrhage can be caused by chronic hypertension or brain trauma, or it can be drug induced, e.g. by antiplatelet treatment (e.g. acetylsalicylic acid) or by anticoagulation treatment (e.g. vitamin K antagonists like phenprocoumon), or it can occur spontaneously in hemorrhagic stroke. Non-traumatic intracerebral hemorrhage is a spontaneous bleeding into the brain tissue. A cerebral hemorrhage is an intra-axial hemorrhage; that is, it occurs within the brain tissue rather than outside of it. There are two main kinds of intra-axial hemorrhages: intraparenchymal hemorrhage and intraventricular hemorrhage (blood in the ventricular system). The other category of intracranial hemorrhage is extra-axial hemorrhage, such as epidural, subdural, and subarachnoid hematomas, which all occur within the skull but outside of the brain tissue.

A subarachnoidal hemorrhage is bleeding into the subarachnoid space—the area between the arachnoid membrane and the pia mater surrounding the brain. This may occur spontaneously, usually from a ruptured cerebral aneurysm, or may result from head injury.

A perinatal stroke as used in the present invention is a focal disease of brain blood vessels that lead to injury in the brain during the fetal or newborn period. Perinatal refers to the timeframe that extends all the way from the middle of pregnancy (fetal life) through birth and the first month of life. Therefore a perinatal stroke means a stroke that occurs in a baby anywhere from after 28 weeks of pregnancy up to 28 days after birth. In some cases, this can lead to childhood epilepsy.

A traumatic brain injury (TBI), also known as intracranial injury, according to the present invention occurs when an external force traumatically injures the brain. TBI can be classified based on severity, mechanism (closed or penetrating head injury), or other features (e.g. occurring in a specific location or over a widespread area) and can cause a host of physical, cognitive, social, emotional, and behavioral effects, and outcome can range from complete recovery to permanent disability or death. Traumatic brain injury is defined as damage to the brain resulting from external mechanical force, such as rapid acceleration or deceleration, impact, blast waves, or penetration by a projectile. Brain function is temporarily or permanently impaired and structural damage may or may not be detectable with current technology.

The term "spinal cord injury" (SCI) as use herein refers to any injury to the spinal cord that is caused by trauma instead of disease. Depending on where the spinal cord and nerve roots are damaged, the symptoms can vary widely, from pain to paralysis to incontinence. Spinal cord injuries are described at various levels of "incomplete", which can vary from having no effect on the patient to a "complete" injury which means a total loss of function. Spinal cord injuries have many causes, but are typically associated with major trauma from e.g. motor vehicle accidents, falls, sports injuries, and violence.

Diabetes mellitus, often simply referred to as diabetes, is a group of metabolic diseases in which a person has high blood sugar, either because the body does not produce enough insulin, or because cells do not respond to the insulin that is produced. Significant changes regarding the blood brain barrier occur which affect the barrier effect as well as the transport functions.

Multiple sclerosis (MS, known as disseminated sclerosis or encephalomyelitis disseminata) is an inflammatory disease in which the fatty myelin sheaths around the axons of the brain and spinal cord are damaged, leading to demyelination and scarring as well as a broad spectrum of signs and symptoms. MS is an infection of the CNS, in which lymphocytes and macrophages are infiltrated in the CNS.

Meningitis is an inflammation of the protective membranes covering the brain and spinal cord, known collectively as the meninges. The inflammation may be caused by infection with viruses, bacteria, or other microorganisms, and less commonly by certain drugs. Meningitis can be life-threatening because of the inflammation's proximity to the brain and spinal cord.

Human immunodeficiency virus (HIV) is a lentivirus (a member of the retrovirus family) that causes acquired immunodeficiency syndrome (AIDS), a condition in humans in which progressive failure of the immune system allows life-threatening opportunistic infections and cancers to thrive. The HI viruses break through the blood brain barrier shortly after the infection.

A brain tumor is an intracranial solid neoplasm, a tumor (defined as an abnormal growth of cells) within the brain or the central spinal canal.

In certain embodiments of the invention the subject having the initial injury is a subject who is not congenitally deficient in C1-inhibitor, i.e. the C1-inhibitor is not administered to a subject who has a congenital deficiency of C1 esterase inhibitor.

In a preferred embodiment of the invention the C1-inhibitor is used to prevent the formation and/or to reduce the size of a secondary edema in a human, i.e. a preferred subject of the invention is a human being. But according to the invention the C1-inhibitor can also be administered to a subject which is an animal, preferably a domestic animal, more preferably a dog, a cat or a horse.

In certain embodiments, a pharmaceutical composition comprising C1-INH is prepared for use in the treatment of secondary edema of the CNS or brain ischemia-reperfusion injury and/or for treating an increased permeability of the blood brain barrier or the blood spinal cord barrier. Methods of formulating pharmaceutical compositions comprising C1-INH are known in the art. For example, if a powder or lyophilized form of C1-INH (e.g., by freeze drying) is provided and an aqueous pharmaceutical is desired, the powder can be dissolved by mixing with aqueous components of the pharmaceutical formulation and stirred using suitable techniques such as vortexing or gentle agitation. In other embodiments, C1-INH is provided in lyophilized form and combined with aqueous pharmaceutical components (e.g., additional active components or inactive components such as fillers, stabilizers, solvents, or carriers) prior to administration.

In certain embodiments, a pharmaceutical composition can comprise at least one additive such as a filler, bulking agent, buffer, stabilizer, or excipient. Standard pharmaceutical formulation techniques are well known to persons skilled in the art (see, e.g., 2005 *Physicians' Desk Reference®*, Thomson Healthcare: Montvale, N. J., 2004; *Remington: The Science and Practice of Pharmacy*, 20th ed., Gennado et al., Eds. Lippincott Williams & Wilkins: Philadelphia, Pa., 2000). Suitable pharmaceutical additives include, e.g., mannitol, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. In certain embodiments, the pharmaceutical compositions may also contain pH buffering reagents and wetting or emulsifying agents. In further embodiments, the compositions may contain preservatives or stabilizers.

The formulation of pharmaceutical compositions may vary depending on the intended route of administrations and other parameters (see, e.g., Rowe et al., *Handbook of Pharmaceutical Excipients*, 4th ed., APhA Publications, 2003). In some embodiments, the pharmaceutical composition may be a lyophilized cake or powder. The lyophilized composition may be reconstituted for administration by intravenous injection, for example with Sterile Water for Injection, USP. In other embodiments, the composition may be a sterile, non-pyrogenic solution. In still further embodiments, the composition is delivered in powder form in a pill or tablet.

The described pharmaceutical compositions may comprise C1-INH as the sole active compounds or may be delivered in combination with at least one other compound, composition, or biological material. Examples of such compounds include vitamins, antibiotics, or compounds intended to remove or inhibit blood clot formation in the brain (e.g., tissue plasminogen activator, acetylsalicylic acid, clopidogrel, or dipyridamole).

Also disclosed are kits for the treatment of secondary edema of the CNS as well as for the treatment of brain ischemia-reperfusion injury or for treating an increased permeability of the blood brain barrier or the blood spinal cord barrier. In certain embodiments, the kits comprise (a) C1-INH, (b) instructions for use in the treatment of secondary edema of the CNS or brain ischemia-reperfusion injury or for use in the treatment of an increased permeability of the blood brain barrier or the blood spinal cord barrier and optionally (c) at least one further therapeutically active compound or drug. The C1-INH component may be in liquid or solid form (e.g. after lyophilization). If in liquid form, the C1-INH may comprise additives such as stabilizers and/or preservatives such as proline, glycine, or sucrose or other additives that enhance shelf-life.

In certain embodiments, the kit may contain additional compounds such as therapeutically active compounds or drugs that are to be administered before, at the same time or after administration of the C1-INH. Examples of such compounds include vitamins, antibiotics, anti-viral agents, etc. In other embodiments, compounds intended to remove or inhibit blood clot formation in the brain (e.g., tissue plasminogen activator, acetylsalicylic acid, clopidogrel, or dipyridamole) can be included with the kit.

In various embodiments, instructions for use of the kits will include directions to use the kit components in the treatment of secondary edema of the CNS or brain ischemia-reperfusion injury or for treating an increased permeability of the blood brain barrier or the blood spinal cord barrier. The instructions may further contain information regarding how to prepare (e.g. dilute or reconstitute, in the case of freeze-dried protein) the C1-Inhibitor. The instructions may further include guidance regarding the dosage and frequency of administration.

A formulation of the C1-inhibitor can be delivered to the individual by any pharmaceutically suitable means of administration. Various delivery systems are known and can be used to administer the composition by any convenient route. In a preferred embodiment the formulation of the C1-inhibitor is administered systemically. For systemic use, the therapeutic protein is formulated for parenteral or enteral (e.g., oral, vaginal or rectal) delivery according to conventional methods. A parenteral administration may include, without limitation, intravenous, subcutaneous, intramuscular, intraperitoneal, intracerebral, subdural, by intrathecal injection or by an injection directly into the brain, intrapulmonar, transdermal or intranasal administration. The most preferential route of administration is intravenous administration. The formulations can be administered continuously by infusion or by bolus injection. Some formulations encompass slow release systems.

In certain embodiments regarding the treatment of a secondary edema, the C1-INH is administered 5, 10, 20, 30, 40, or 50 minutes, or 1, 2, 3, 4, 5, 6, 7, 8, 9, 10, 11, 12, 13, 14, 15, 16, 17, 18, 19, 20, 21, 22, 23, 24, 36, 48, 72, 96, 120, or 240 hours (or at any time in between) after the initial injury has started. In a preferred embodiment the administration take place at the latest 10 days after the initial injury, preferably at the latest 5 days, more preferably at the latest 3 days, more preferably at the latest 1 day, more preferably at the latest 12 hours, more preferably at the latest 6 hours, more preferably at the latest 3 hours, more preferably at the latest 1 hour, more preferably at the latest 30 minutes and even more preferably at directly after the initial injury (or at any time in between).

With regard to the long half-life of human C1 esterase inhibitor and/or the prophylactic treatment the preferred administration should be as quick as possible following the occurrence of the initial injury.

In other preferred embodiments treatment with C1-INH can be started immediately or up to ten days after start of reperfusion following the occlusion, which was caused by the initial insult. Preferably, such treatment occurs as soon as possible following the start of reperfusion. In certain embodiments, treatment occurs 5, 10, 20, 30, 40, or 50 minutes, or 1, 2, 3, 4, 5, 6, 7, 8, 9, 10, 11, 12, 13, 14, 15, 16, 17, 18, 19, 20, 21, 22, 23, 24, 36, 48, 72, 96, 120, or 240 hours (or at any time in between) after the start of reperfusion following the initial injury (or at any time in between). In a preferred embodiment the administration take place at latest 10 days after start of reperfusion following the initial injury, preferably at latest 5 days, more preferably at latest 3 days, more preferably at latest 1 day, more preferably at latest 12 hours, more preferably at latest 6 hours, more preferably at latest 3 hours, more preferably at latest 1 hour, more preferably at latest 30 minutes and even more preferably at directly after start of reperfusion following the initial injury.

In certain embodiments regarding the treatment of brain ischemia-reperfusion injury with the plasma-derived C1-inhibitor the treatment can be started 30 minutes up to ten days after start of reperfusion. In preferred embodiments, treatment occurs 30, 40, or 50 minutes, or 1, 2, 3, 4, 5, 6, 7, 8, 9, 10, 11, 12, 13, 14, 15, 16, 17, 18, 19, 20, 21, 22, 23, 24, 36, 48, 72, 96, 120, or 240 hours after start of reperfusion (or at any time in between). In other embodiments the administration take place not later than 10 days after start of reperfusion, preferably not later than 5 days, more preferably not later than 3 days, more preferably not later than 1 day, more preferably not later than 12 hours, more preferably not later than 6 hours, more preferably not later than 3 hours, more preferably not later than 1 hour, more preferably not later than 45 minutes and even more preferably not later than 30 minutes after start of reperfusion (or at any time in between). Preferably, such treatment occurs between 30 minutes and 10 days after start of reperfusion, more preferably between 30 minutes and 5 days, more preferably between 30 minutes and 3 days and more preferably between 30 minutes and 1 day after start of reperfusion (or at any time period in between).

Administration to a patient may occur in a single dose or in repeated administrations, and in any of a variety of physiologically acceptable salt forms, and/or with an acceptable pharmaceutical carrier and/or additive as part of a pharmaceutical composition. Therefore in certain embodiments the C1-inhibitor is administered (i) in a single dose as injection or infusion, or (ii) in multiple doses, preferably in two doses, each as injection or infusion, or (iii) as a long-term infusion or application. The long-term-infusion/application is administered over a period of time, preferably over a period of 30 minutes to 2 weeks, more preferably 30 minutes to 1 week, more preferably 30 minutes to 6 days, more preferably 30 minutes to 5 days, more preferably 30 minutes to 4 days, more preferably 30 minutes to 3 days, more preferably 30 minutes to 2 days, more preferably 30 minutes to 1 day, more preferably 30 minutes to 12 hours, more preferably 30 minutes to 6 hours (or any time period in between).

In a preferred embodiment the administration to a patient occurs in a double dose, once after the initial insult and before the start of reperfusion and once after the start of reperfusion following the initial injury.

The composition comprising C1-INH may be administered to a patient in therapeutically effective amounts. Generally, a therapeutically effective amount may vary with the subject's age, general condition, and gender, as well as the severity of the medical condition in the subject. The dosage may be determined by a physician and adjusted, as necessary, to suit the observed effects of the treatment. In certain embodiments, the dose of C1-INH may range from approximately 1 U/kg to 5000 U/kg of bodyweight. In various embodiments, the dose of C1-INH is 1, 5, 7.5, 10, 15, 20, 25, 30, 50, 75, 100, 125, 150, 175, 200, 225, 250, 275, 300, 325, 350, 375, 400, 450, 500, 1000, 1500, 2000, 2500, 3000, 3500, 4000, or 4500 U/kg of bodyweight (or any value in between). Exemplary therapeutic ranges for C1-INH administration are also disclosed in U.S. Pat. No. 5,939,389, the disclosure of which is incorporated in its entirety. Preferably the C1-inhibitor is administered in a dose of 1 to 1000 units per kg body weight, more preferably 5 to 500 units per kg body weight, more preferably 10 to 200 units per kg body weight and most preferably in a dose of 20 to 100 units per kg body weight.

The administered pharmaceutical compositions may comprise C1-INH as the sole active compounds or may be delivered in combination with at least one other compound, composition, or biological material. Examples of such compounds include vitamins, antibiotics, or compounds intended to remove or inhibit blood clot formation in the brain (e.g., tissue plasminogen activator, acetylsalicylic acid, clopidogrel, or dipyridamole).

In a further embodiment of the present invention a method of preventing the formation and/or reducing the size of a secondary edema of the central nervous system (CNS) in a subject wherein the subject has or has had at least one disorder selected from the group consisting of stroke, ischemic stroke, hemorrhagic stroke, perinatal stroke, traumatic brain injury, and spinal cord injury. Preferably said secondary edema of the CNS is a secondary brain edema or a secondary spinal cord edema.

Figure 1A:
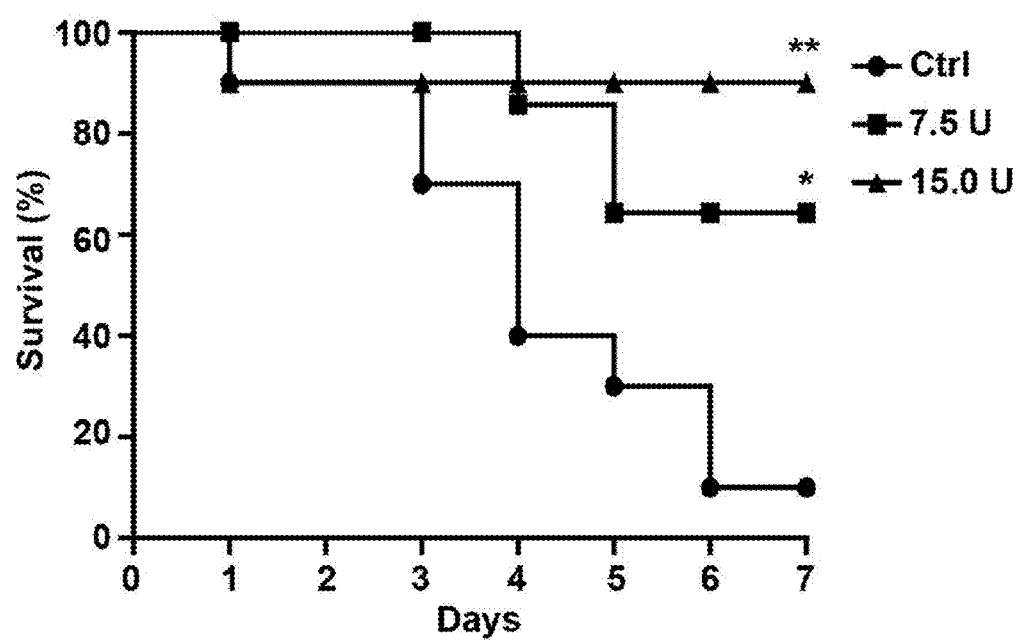
FIGS. 1A and 1B: C1-INH reduces mortality and improves functional outcome after acute ischemic stroke in mice. (a) Mortality in C1-INH-treated mice (7.5 U or 15.0 U, respectively) and controls until day 7 after tMCAO (n=10/group); **p=0.0087, *p=0.0215, log-rank test compared with control mice. (b) Long-term functional outcome (Bederson score) on day 5 after tMCAO (n=3-9/group); **p<0.01, Kruskal-Wallis test followed by Dunn's multiple comparison test.

The examples illustrate the present invention while in no way limiting it.

Ischemia Model.

C57Bl/6 mice and CD rats were included in the study which was conducted in accordance with institutional guidelines for the use of experimental animals, and the protocols were approved by governmental authorities (Regierung von Unterfranken, Wurzburg, Germany; Regierungsprasidium Giessen, Germany). Focal cerebral ischemia was induced for 60 min (6-8 weeks or 20 weeks old C57Bl/6 mice) or 90 min (7-9 weeks old CD rats) by transient middle cerebral artery occlusion (tMCAO) using the intraluminal filament technique (Longa, E. Z., Weinstein, P. R., Carlson, S., & Cummins, R., *Reversible middle cerebral artery occlusion without craniectomy in rats*. Stroke 1989; 20 (1):84-91; Kleinschnitz et al *Stroke* 2011). Animals were controlled for critical physiological parameters that can affect stroke outcome (e.g. cerebral blood flow). All stroke experiments were performed in accordance with the recently published ARRIVE guidelines (www.nc3rs.org/ARRIVE). Animals were randomly assigned to the operators by an independent person not involved in data acquisition and analysis. We performed surgery and evaluation of all read-out parameters while being blinded to the experimental groups. The detailed study design including exclusion criteria is given in the below.

Induction of Cerebral Ischemia in Mice.

Focal cerebral ischemia was induced in 6-8-weeks or 20 weeks old mice by 60 min transient middle cerebral artery occlusion (tMCAO) as described (Kleinschnitz et al., *J Exp Med* 2006; *PloS Biol* 2010). Mice were anesthetized with 2.5% isoflurane (Abbott, Wiesbaden, Germany) in a 70% $N_2O$/30% $O_2$ mixture. Core body temperature was maintained at 37° C. throughout surgery by using a feedback-controlled heating device. Following a midline skin incision in the neck, the proximal common carotid artery and the external carotid artery were ligated and a standardized silicon rubber-coated 6.0 nylon monofilament (6021; Doccol Corp., Redlands, Calif., USA) was inserted and advanced via the right internal carotid artery to occlude the origin of the right MCA. The intraluminal suture was left in situ for 60 minutes. Then animals were re-anesthetized and the occluding monofilament was withdrawn to allow for reperfusion.

Assessment of Functional Outcome in Mice.

On day 1 (24 h post initial insult) and day 5 after tMCAO, neurological deficits were scored and quantified according to Bederson (Bederson J B, Pitts L H, Tsuji M, Nishimura M C, Davis R L, Bartkowski H. *Rat middle cerebral artery occlusion: evaluation of the model and development of a neurologic examination. Stroke.* 1986; 173:472-476): 0, no deficit; 1, forelimb flexion; 2, as for 1, plus decreased resistance to lateral push; 3, unidirectional circling; 4, longitudinal spinning; 5, no movement. For the grip test (Moran P M, Higgins L S, Cordell B, Moser P C. *Age-related learning deficits in transgenic mice expressing the 751-amino acid isoform of human beta-amyloid precursor protein. Proc Natl Acad Sci USA.* 1995; 9212:5341-5345), the mouse was placed midway on a string between two supports and rated as follows: 0, falls off; 1, hangs on to string by one or both fore paws; 2, as for 1, and attempts to climb on to string; 3, hangs on to string by one or both fore paws plus one or both hind paws; 4, hangs on to string by fore and hind paws plus tail wrapped around string; 5, escape (to the supports).

Induction of Cerebral Ischemia in Rats.

7-9 weeks old rats were subjected to 90 min of tMCAO using an intraluminal filament technique (Longa, E. Z., Weinstein, P. R., Carlson, S., & Cummins, R., *Reversible middle cerebral artery occlusion without craniectomy in rats. Stroke* 1989; 20 (1):84-91). In detail, anesthesia was induced in spontaneously breathing animals in an isoflurane chamber with 5% isoflurane (CP Pharma, Burgdorf, Germany) and was subsequently maintained with 2.5% isoflurane via a face mask. During surgery, animals were placed on a heating device to ensure normothermia (37° C.). Following a midline skin incision in the neck, the left common carotid artery and external carotid artery were isolated and ligated. Following arteriotomy a standardized silicon-coated 4.0 nylon monofilament (Ethilon®; Johnson & Johnson, St-Stevens-Woluwe, Belgium) with its tip blunted by heat was inserted into the internal carotid artery and advanced cranially to the origin of the middle cerebral artery until a gentle resistance was felt. The occluding filament was left in situ for 90 minutes. Then animals were re-anesthetized and the occluding monofilament was withdrawn to allow for reperfusion.

C1-INH Treatment.

1 h or 6 h after the induction of tMCAO (initial insult) mice received a single intravenous injection of plasmatic human C1-INH (Berinert® P, CSL Behring GmbH, Marburg, Germany) at a dose of 7.5 units (U) or 15.0 U diluted in 150 µl carrier solution (isotonic saline). The respective doses were chosen based on previously published work in rodent models of cerebral ischemia and 15.0 U corresponds to the amount of C1-INH required to obtain 90% to 95% inhibition of complement haemolytic activity in mice (Longhi L et al., *Crit Care Med* 2009; Storini C et al., *Neurobiol Dis,* 2005). In rats, C1-INH was intravenously injected 90 min after the induction of tMCAO (immediately after induction of reperfusion) at a dose of 20 U/kg body weight. Control mice and rats received equal volumes of isotonic saline (vehicle).

Stroke Study Design.

Vehicle-treated mice or rats or mice or rats receiving C1-INH were randomly assigned to the operators by an independent person not involved in data acquisition and analysis. We performed surgery and evaluation of all read-out parameters while blinded to the experimental groups. The following conditions excluded animals from end-point analyses (exclusion criteria):
1. Death within 24 h after MCAO
2. Subarachnoidal hemorrhage (SAH) (as macroscopically assessed during brain sampling or by MRI)
3. Bederson score=0 (24 h after tMCAO, mice only)

Drop-out rates were evenly distributed between the groups.

Determination of Blood-Brain-Barrier Leakage and Brain Edema.

To determine blood-brain-barrier leakage 100 µl of 2% Evan's Blue tracer (Sigma Aldrich, Germany) diluted in 0.9% NaCl was i. v. injected 1 h after the induction auf tMCAO (Austinat et al., *Stroke* 2011). After 24 h C1-INH-treated mice and controls were transcardially perfused with 4% paraformaldehyd (PFA) and brains were quickly removed and cut in 2 mm thick coronal sections using a mouse brain slice matrix (Harvard Apparatus, Holliston, Mass., USA). Planimetric measurements (ImageJ software, National Institutes of Health, USA) of the brain parenchyma stained by Evan's Blue were performed to estimate blood-brain-barrier damage.

To assess the extent of secondary brain edema, C1-INH-treated mice or controls were sacrificed 24 h after tMCAO. Brains were removed, hemispheres separated, and weighed to assess the wet weight (WW). Thereafter, the hemispheres were dried for 72 h at 60° C. and the dry weight (DW) was determined. Hemispheric water content (%) was calculated using the following formula: $((WW-DW)/WW) \times 100$ (Austinat et al., *Stroke* 2009).

In rats, the extent of secondary brain edema was calculated by planimetry from TTC-stained brain sections according to the following equation:

$$\text{Brain edema area (\%)} = [(AL+Al+AC) \times 100/(AC \times 2)] - 100,$$

whereas AL represents the total area of TTC-negative (ischemic) brain tissue, Al represents the total area of viable tissue of the ipsilateral (stroked) hemisphere, and AC represents the total area of the contralateral (healthy) hemisphere.

TTC (2,3,5-triphenyltetrazolium chloride) staining, needed for calculation of brain edema in rats, was performed using the following protocol: Rats were sacrificed 24 h after tMCAO. Brains were quickly removed and cut in six 2-mm thick coronal sections using a razor blade (VWR International GmbH, Darmstadt, Germany). The slices were stained for 15 min at 37° C. with 2% TTC (Merck Eurolab GmbH, Darmstadt, Germany) in PBS to visualize the infarctions (Bederson J B, Pitts L H, Germano S M, Nishimura M C, Davis R L, Bartkowski H M. *Evaluation of 2,3,5-triphenyltetrazolium chloride as a stain for detection and quantification of experimental cerebral infarction in rats. Stroke.* 1986; 176:1304-1308).

Histology and Immunohistochemistry.

Cryo-embedded brains were cut into 10-µm thick slices and fixed in acetone for staining of neutrophilic granulocytes or in 4% PFA in PBS for staining of microglia/macrophages and occludin. Blocking of epitopes was achieved by pre-treatment with bovine serum albumin (BSA) in PBS for 45 min to prevent unspecific binding. For staining of invading immune cells (Austinat et al., 2009) rat anti-mouse Ly-6B.2 alloantigen (neutrophilic granulocytes; MCA771GA, AbD Serotec, Germany) at a dilution of 1:1000 and rat anti-mouse CD11 b (microglia/macrophages; MCA711, AbD Serotec, Germany) at a dilution of 1:100 in PBS containing 1% BSA was added overnight at 4° C. Afterwards, slides were incubated with a biotinylated anti-rat IgG (BA-4001, Vector Laboratories, USA) diluted 1:100 in PBS containing 1% BSA for 45 min at room temperature. Following treatment with Avidin/Biotin blocking solution (Avidin/Biotin Blocking Kit, Sp-2001, Vector Laboratories, Inc., California, USA) to inhibit endogenous peroxidase activity, the secondary antibody was linked via streptavidin to a biotinylated peroxidase (POD) according to the manufacturer's instructions (Vectorstain ABC Kit, Peroxidase Standard PK-4000, Vector Laboratories, Inc., California, USA). Antigens were visualized via POD using the chromogen 3,3'-Diaminobenzidin (DAB) (Kem-En-Tec Diagnostics, Denmark). For quantification of immune cells identical brain sections (thickness 10-µm) at the level of the basal ganglia (0.5 mm anterior from bregma) from C1-INH-treated mice and controls were selected and cell counting was performed from 5 subsequent slices (distance 10 µm) from 4 different animals under a Nikon microscope Eclipse 50i (Nikon, Germany) (Austinat et al., 2009).

For immunofluorescence staining against occludin rabbit anti-mouse occludin antibody (ab 31721, Abcam, UK) was applied overnight (4° C.) at a dilution of 1:100 in PBS containing 1% BSA. Proteins were detected with Cy3-labeled goat anti-rabbit secondary antibodies at a dilution of 1:300 in 1% BSA in PBS. For staining of DNA a fluorescent Hoechst dye (Hoechst 33342, Sigma-Aldrich, Germany) was added for 30 min at a concentration of 0.4 mg/ml. sections were analyzed under an Axiophot 2 (Zeiss, Germany).

For calculation of the thrombosis index the whole brain was sliced 24 h after tMCAO. H&E staining was performed according to standard procedures. For quantification, stainings were examined in a blinded fashion under a microscope (Axiophot2, Carl Zeiss AG) equipped with a CCD camera (Visitron Systems). The number of occluded blood vessels within the ischemic basal ganglia was counted in every tenth slice for control mice, or mice treated with 7.5 U C1-INH or 15.0 U C1-INH, respectively, using a 40-fold magnification.

Negative controls for all histological experiments included omission of primary or secondary antibody and produced no detectable signal (not shown).

PCR studies.

Tissue homogenization, RNA isolation and Real-time RT-PCR were performed as described (Austinat et al., *Stroke* 2009). Total RNA was prepared with a Miccra D-8 power homogenizer (ART, Germany) using the TRIzol Reagent® (Invitrogen, Germany) and was quantified spectrophotometrically. Then, 1 µg of total RNA were reversely transcribed with the TaqMan® Reverse Transcription Reagents (Applied Biosystems, Germany) according to the manufacturer's protocol using random hexamers. Relative gene expression levels of endothelin-1 (assay ID: Mm 00438656_m1, Applied Biosystems, Germany) were quantified with the fluorescent TaqMan® technology. GAPDH (TaqMan® Predeveloped Assay Reagents for gene expression, part number: 4352339E, Applied Biosystems, Germany) was used as an endogenous control to normalize the amount of sample RNA. The PCR was performed with equal amounts of cDNA in the StepOnePlus™ Real-Time PCR System (Applied Biosystems, Germany) using the TaqMan® Universal 2×PCR Master Mix (Applied Biosystems, Germany). Reactions (total volume 12.5 µl) were incubated at 50° C. for 2 min, at 95° C. for 10 min followed by 40 cycles of 15 s at 95° C. and 1 min at 60° C. Water controls were included to ensure specificity. Each sample was measured in triplicate and data points were examined for integrity by analysis of the amplification plot. The comparative Ct method was used for relative quantification of gene expression as described (Livak K J, Schmittgen T D. *Analysis of relative gene expression data using real-time quantitative PCR and the 2(−Delta Delta C(T)) Method. Methods.* 2001; 25:402-408).

Western Blot.

Brain cortices or basal ganglia were dissected from native brains and homogenized in RIPA buffer (25 mM Tris pH 7.4, 150 mM NaCl, 1% NP-40) containing 0.1% SDS and 4% proteinase inhibitor (complete protease inhibitor cocktail, Roche). Samples were sonified for 10 sec. Afterwards tissue lysates were centrifuged at 15.000×g for 30 min at 4° C. and supernatants were used for BCA protein assay and subsequent Western blot analysis. The total lysates were treated with 4×SDS-PAGE loading buffer (final conc. 62.5 mM Tris pH 6.8, 3% beta-mercaptoethanol, 8% SDS, 15% glycerol) at 95° C. for 5 min. 20 µg of total protein was electrophoresed and transferred to a PVDF membrane. After blocking for 30 min with blocking buffer (5% nonfat dry milk, 50 mM Tris-HCl pH 7.5, 0.05% Tween-20) membranes were incubated with the primary antibody at 4° C. overnight at the following dilutions: anti-Fibrinogen pAb 1:500 (Acris Antibodies), anti-occludin pAb 1:1000 (Abcam, UK), and anti-Actin mAb 1:75.000 (Dianova). After a washing step with TBS-T (50 mM Tris-HCl pH 7.5, 0.05% Tween-20), membranes were incubated for 1 h with HRP-conjugated donkey anti-rabbit IgG (for fibrinogen and occludin) (Dianova, Germany) or donkey anti-mouse IgG (for actin) (Dianova, Germany) at a dilution of 1:5000 and were finally developed using ECLplus (GE Healthcare) (Kraft et al., *Thrombin-activatable fibrinolysis inhibitor (TAFI) deficient mice are susceptible to intracerebral thrombosis and ischemic stroke. PLoS One* 2010).

Statistics

All results were expressed as mean±standard deviation (s.d.) except for ordinal functional outcome scales which were depicted as scatter plots including median with the 25% percentile and the 75% percentile given in brackets in the text. Numbers of experiments to detect a standardized effect size on infarct volumes ≥0.15 were calculated via a priori power analysis with the following assumptions: $\alpha=0.05$, $\beta=0.2$, mean, standard deviation 10% of the mean. For statistical analysis, the GraphPad Prism 5.0 software package (La Jolla, Calif., USA) was used. Data were tested for Gaussian distribution with the D'Agostino and Pearson omnibus normality test and then analyzed by 1-way ANOVA or in case of measuring the effects of two factors simultaneously 2-way ANOVA with post hoc Bonferroni adjustment for p values. Non-parametric functional outcome scores were compared by Kruskal-Wallis test with post hoc Dunn's multiple comparison test. For comparison of survival curves the Logrank test was used. Rat data were compared by unpaired, two-tailed Student's t-test (stroke size, brain edema) or non-parametric Mann Whitney test (functional scores). P-values <0.05 were considered statistically significant.

Results

The functional outcome and mortality of C1-INH-treated mice and controls over a longer time period after ischemic stroke was determined (FIG. 1*a, b*). Seven days after 60 min of tMCAO, 9 out of 10 control mice (90%) had died, which is in line with previous reports (Kleinschnitz et al., *PLoS*

Figure 1B:
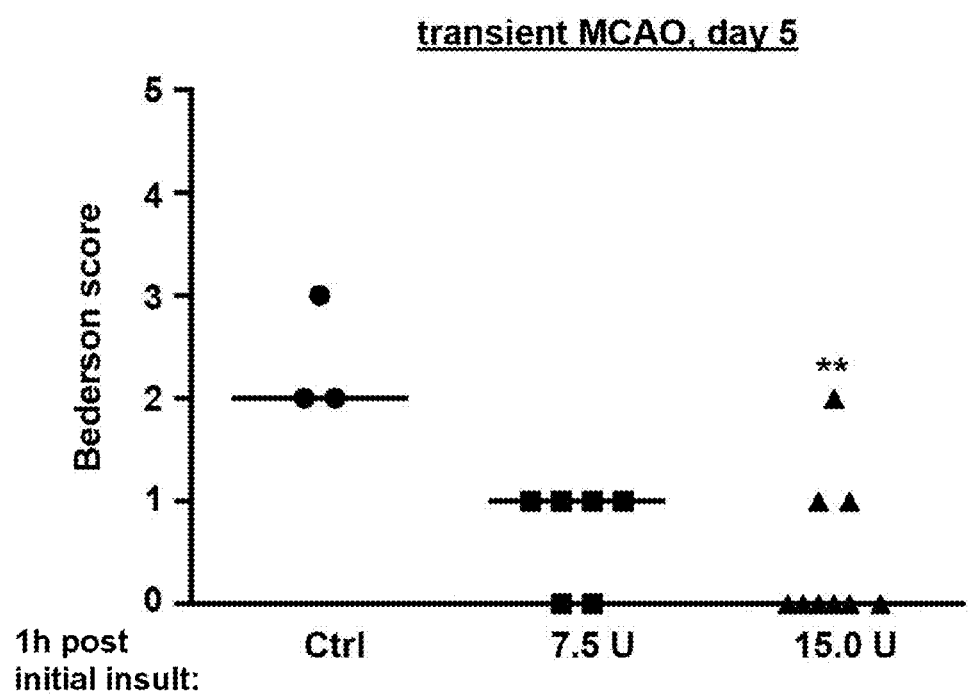

Biol 2010). In contrast, 7 out of 10 mice (70%) treated with 7.5 U C1-INH and 9 out of 10 mice (90%) treated with the higher dose of 15.0 U C1-INH survived until day 7 ($p<0.05$ or $p<0.01$, respectively) (FIG. 1a). In line with these findings, mice receiving 15.0 U C1-INH showed significantly better Bederson scores than controls also at more advanced stages of infarct development, i.e. on day 5 after tMCAO (Bederson score: median 2.0 [2.0, 3.0] [control] vs. 0.0 [0.0, 1.0] [15.0 U], respectively; $p<0.01$) (FIG. 1b).

Figure 2A:
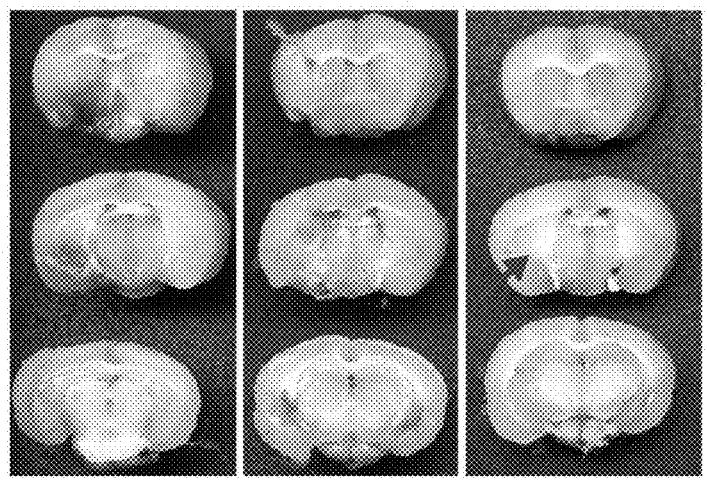
FIGS. 2A-2D: C1-INH shows profound blood-brain-barrier stabilizing and anti-edematous effects in ischemic stroke. (a) Upper panel: Representative corresponding coronal brain sections of control mice (Ctrl) and mice treated 1 h post initial insult with 7.5 U C1-INH or 15.0 U C1-INH on day 1 after tMCAO (24 h post initial insult) after injection of the vascular tracer Evan's blue. Vascular leakage was significantly decreased after C1-INH treatment. Note that Evan's blue extravasation was even nearly absent in areas where infarction was present also in mice receiving C1-INH (basal ganglia, red arrow). Lower panel: Volume of Evan's blue extravasation determined by planimetry in the ischemic hemisphere of treated and untreated mice 24 h after tMCAO (n=7-10/group); *p<0.05, 1-way ANOVA, Bonferroni post-hoc test compared with untreated control mice. (b) Edema formation as measured by the brain water content in the ischemic hemisphere of control mice (Ctrl) and mice treated 1 h post initial insult with 7.5 U C1-INH or 15.0 U C1-INH on day 1 after tMCAO (24 h post initial insult) (n=5/group); *p<0.0001, 1-way ANOVA, Bonferroni post-hoc test compared with untreated control mice. (c) Relative gene expression of endothelin-1 in the cortex and basal ganglia of sham-operated mice, controls (Ctrl) and mice treated 1 h post initial insult with 7.5 U C1-INH or 15.0 U C1-INH (n=6-14/group) 24 h after tMCAO. Note that 15.0 U C1-INH prevented the induction of endothelin-1 in both brain regions; *p<0.0001, ###p<0.0001, 2-way ANOVA, Bonferroni post-hoc test compared with sham-operated mice (cortex (*) or basal ganglia (#), respectively). (d) Western blot analysis of occludin expression in the ischemic basal ganglia on day 1 after tMCAO (24 h post initial insult) in control mice or mice receiving 7.5 U C1-INH or 15.0 U C1-INH, respectively (treatment 1 h post initial insult) (n=4/group), *p<0.05, 1-way ANOVA, Bonferroni post-hoc test compared with untreated mice.
Figure 2A:
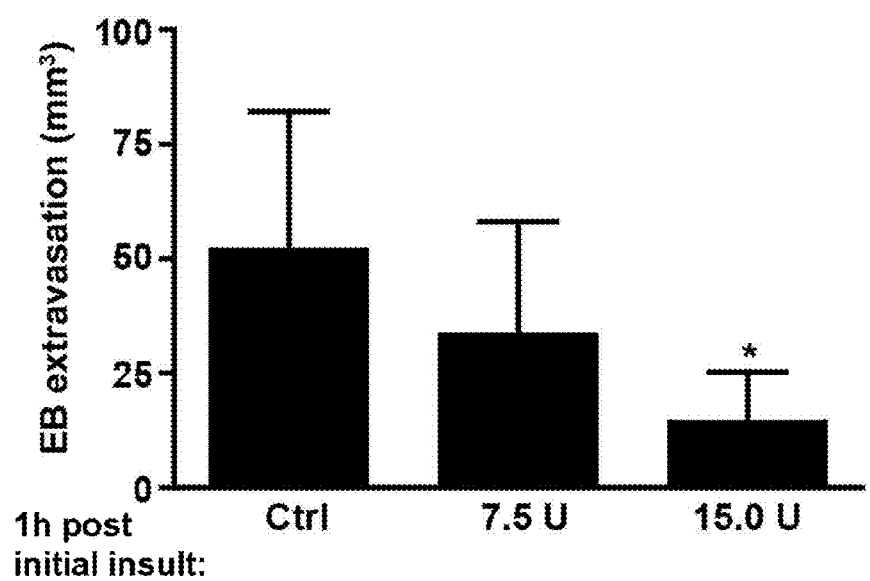
Figure 2B:
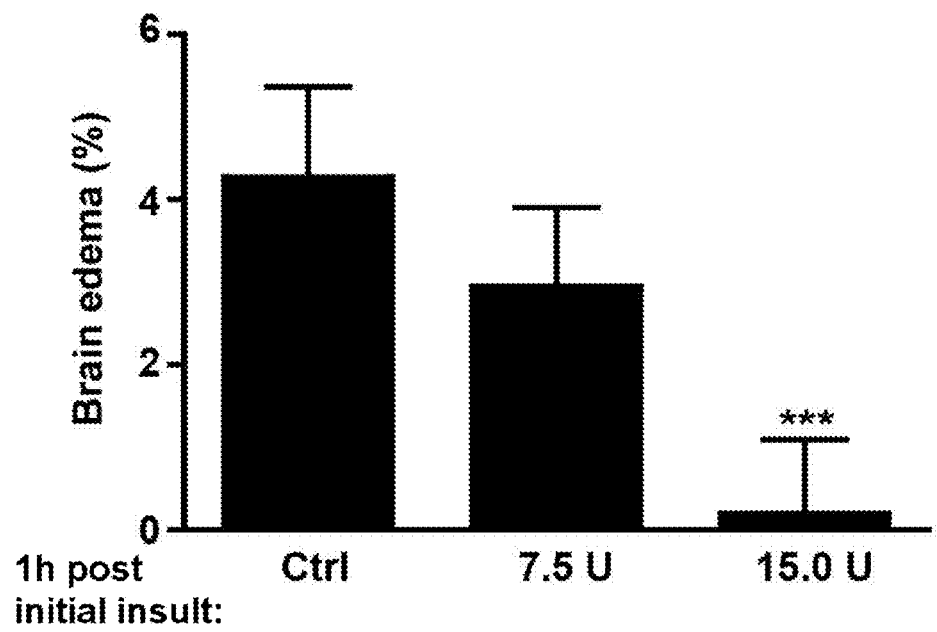
Figure 3:
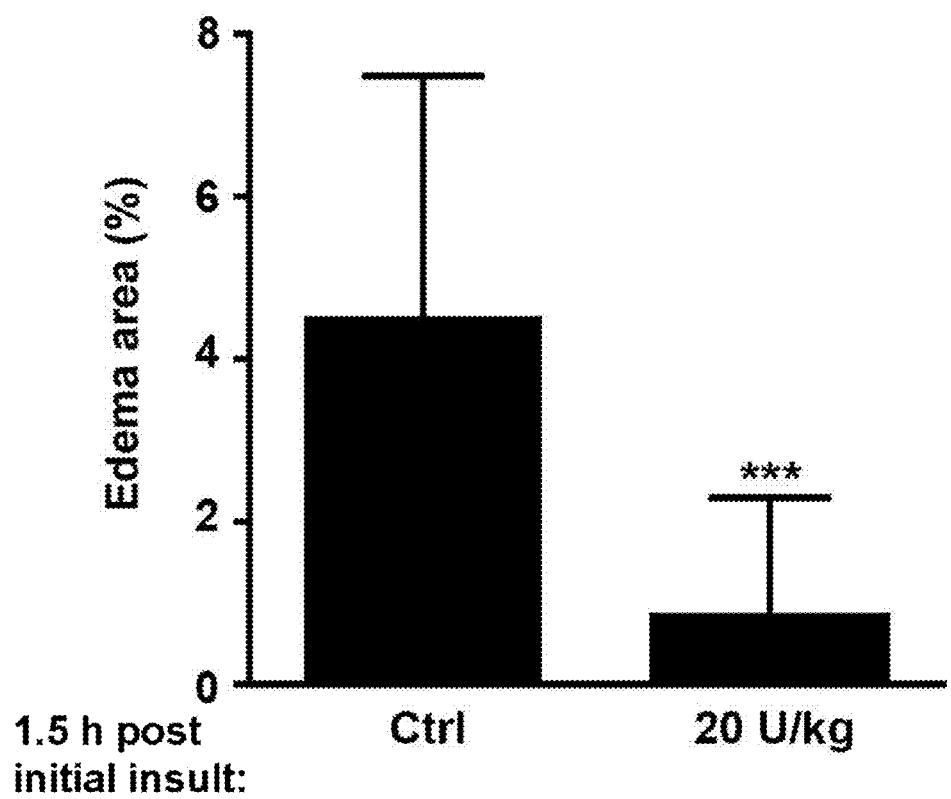
FIG. 3: C1-INH treatment reduces brain edema formation upon stroke in rats. Rats were subjected to 90 min of tMCAO and treated with 20 U/kg C1-INH immediately after reperfusion. The extent of brain edema was calculated by planimetry from TTC-stained brain sections on day 1 (24 h post initial insult) (n=15/group); ***p<0.0001, two-tailed Student's t-test compared with vehicle-treated controls.

C1-INH plays an important role in the regulation of vascular permeability and suppression of inflammation by inactivating key proteases of the contact-kinin system such as factor XIIa or plasma kallikrein (Alvin E. Davis III, Pedro Mejia, Fengxin Lu, *Molecular Immunology* 2008). Consequently, the extent of blood-brain-barrier damage and edema formation in the ischemic hemispheres was addressed. On day 1 after tMCAO the integrity of the blood-brain-barrier as determined by the volume of the vascular tracer Evan's Blue leaking into the brain parenchyma was preserved in mice treated with 15.0 U C1-INH 1 h post stroke and less pronounced also after injection of 7.5 U C1-INH in comparison with treatment naïve controls (mean $51.6\pm30.6$ mm$^3$ [control] vs. $33.1\pm25.0$ mm$^3$ [7.5 U] or $13.9\pm11.4$ mm$^3$ [15.0 U], respectively; $p<0.05$ [control vs. 15.0 U]) (FIG. 2a). This finding correlated with dramatically less secondary brain edema formation (wet/dry weight method) following therapeutic C1-INH application (mean $4.3\pm1.1\%$ [control] vs. $2.9\pm1.0\%$ [7.5 U] or $0.2\pm0.9\%$ [15.0 U], respectively; $p<0.0001$ [control vs. 15.0 U]) (FIG. 2b), a result that could also be confirmed in rats (FIG. 3). Importantly, almost no blood-brain-barrier disruption was found in the brain regions (basal ganglia) where infarcts were regularly present also in C1-INH-treated mice (FIG. 2a, arrow). This indicates that the lesser edema seen in the C1-INH group was a specific phenomenon and mechanistically relevant but not simply due to smaller infarct volumes in these animals.

Figure 2C:
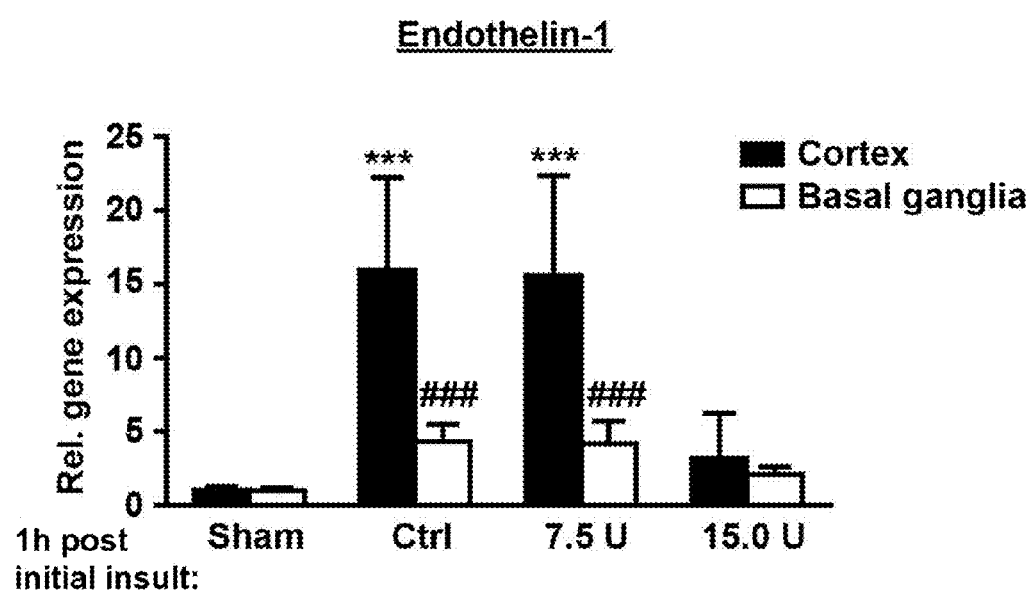

The expression of endothelin-1 in the ischemic brains of C1-INH-treated mice and controls has also been analyzed. Endothelin-1 has been shown to be critically involved in regulating vascular integrity and edema formation under various pathophysiological conditions including ischemic stroke (Matsuo Y, Mihara Si, Ninomiya M, Fujimoto M. *Protective effect of endothelin type A receptor antagonist on brain edema and injury after transient middle cerebral artery occlusion in rats. Stroke.* 2001; 32:2143-2148; Barone F C, Globus M Y, Price W J, White R F, Storer B L, Feuerstein G Z, Busto R, Ohlstein E H. *Endothelin levels increase in rat focal and global ischemia. J Cereb Blood Flow Metab.* 1994; 14:337-342). 24 h after tMCAO endothelin-1 mRNA levels were significantly elevated in the cortices and basal ganglia of vehicle-treated mice and mice receiving 7.5 U C1-INH compared with sham operated mice (relative gene expression cortex: $1.0\pm0.2$ [sham] vs. $16.0\pm6.3$ [control] or $15.6\pm6.8$ [7.5 U], respectively, $p<0.0001$; relative gene expression basal ganglia: $1.0\pm0.2$ [sham] vs. $4.3\pm1.2$ [control] or $4.2\pm1.5$ [7.5 U], respectively, $p<0.0001$) (FIG. 2c). In contrast, no significant induction of endothelin-1 transcripts was observed in either brain region after treatment with 15.0 U C1-INH ($p>0.05$). Again, endothelin-1 expression remained low also in the basal ganglia after high-dose (15.0 U) C1-INH treatment (FIG. 2c) although the basal ganglia were uniformly included into the infarcted areas in all animals.

Figure 2D:
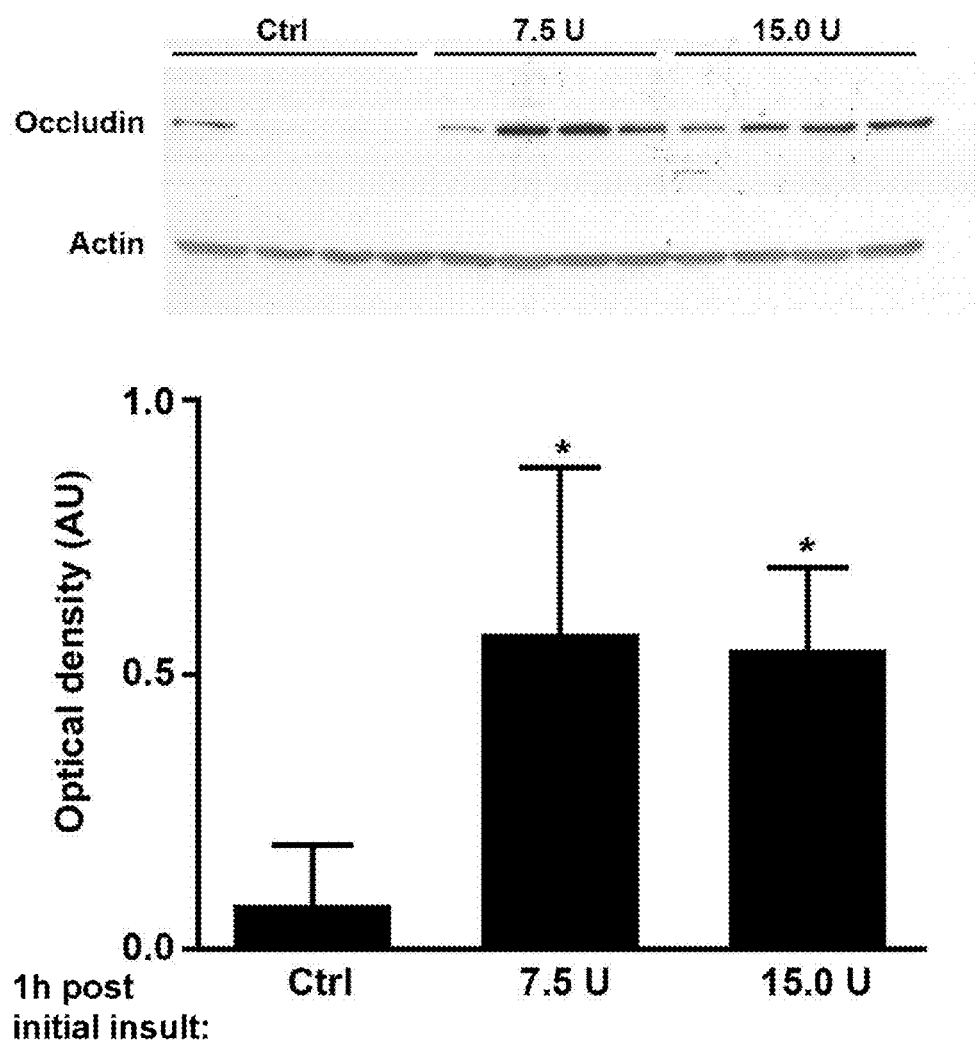

In line with a blood-brain-barrier stabilizing effect of C1-INH in stroke immunoreactivity against the tight junction protein occludin was preserved in vessels of the ischemic basal ganglia from mice treated with 15.0 U C1-INH but was down-regulated in control mice or mice receiving 7.5 U C1-INH as demonstrated by immunohistochemistry. To quantify occludin protein expression in more detail Western blot analysis have been also performed (FIG. 2d). Again, the amount of occludin on day 1 after tMCAO in the ischemic basal ganglia from untreated mice was low (optical density: $0.08\pm0.10$). In contrast, significantly more occludin protein was detectable after treatment with 7.5 U (optical density: $0.6\pm0.3$, $p<0.05$) or 15.0 U (optical density: $0.5\pm0.2$, $p<0.05$) C1-INH, respectively.

C1-INH has been shown to inhibit cell migration from the vasculature to inflammation sites by binding of cell adhesion molecules (Cai S, Davis III, AE, 2004, *J Immunol*). Therefore, the numbers of immune cells invading the ischemic brain by immunocytochemistry have been quantified. 24 h after the induction of tMCAO significantly more neutrophilic granulocytes (mean $299.1\pm138.1$ [control] vs. $107.2\pm109.5$ [15.0 U], $p<0.05$) as well as macrophages/microglia cells (mean $676.3\pm150.4$ [control] vs. $117.1\pm64.9$ [15.0 U], $p<0.0001$) had entered the ischemic basal ganglia of untreated control mice than of mice that had been treated with 15.0 U C1-INH 1 h post stroke. In contrast, the lower dose of 7.5 U C1-INH was unable to reduce cell trafficking after focal cerebral ischemia ($p>0.05$).

Figure 4A:
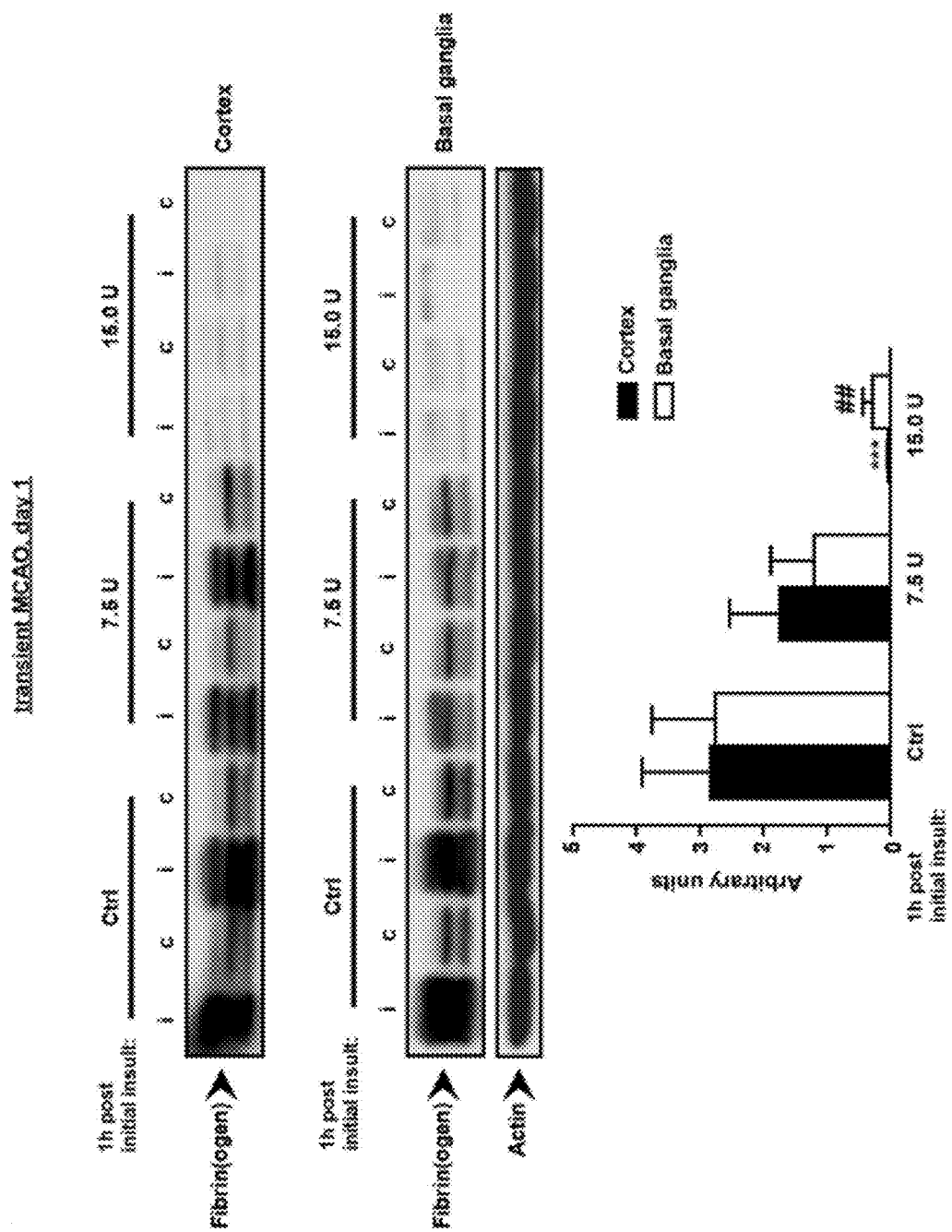
FIGS. 4A and 4B: C1-INH treatment reduces intracerebral thrombus formation after stroke. (a) Upper panel: Accumulation of fibrin(ogen) in the infarcted (i) and contralateral (c) cortices and basal ganglia of control mice (Ctrl) and mice treated with 7.5 U C1-INH or 15.0 U C1-INH as determined by immunoblotting 24 h after tMCAO. Two representative immunoblots of each group are shown. Lower panel: Densitometric quantification of thrombus formation in the mouse groups and brain regions indicated above (n=3-5/group); ***p<0.0001, ##p<0.01, 2-way ANOVA, Bonferroni post-hoc test compared with controls (cortex (*) or basal ganglia (#), respectively). (b) Upper panel: Representative H&E staining from the infarcted basal ganglia of control mice (Ctrl) and mice treated with 15.0 U C1-INH on day 1 after tMCAO. Thrombotic vessels were abundant in control mice (arrowheads) while the microvascular patency was significantly increased in mice receiving 15.0 U C1-INH (arrow) and this was confirmed by calculation of the thrombosis index (n=5/group) (lower panel); *p<0.05, 1-way ANOVA, Bonferroni post-hoc test compared with controls. Scale bar: 100 µm.
Figure 4B:
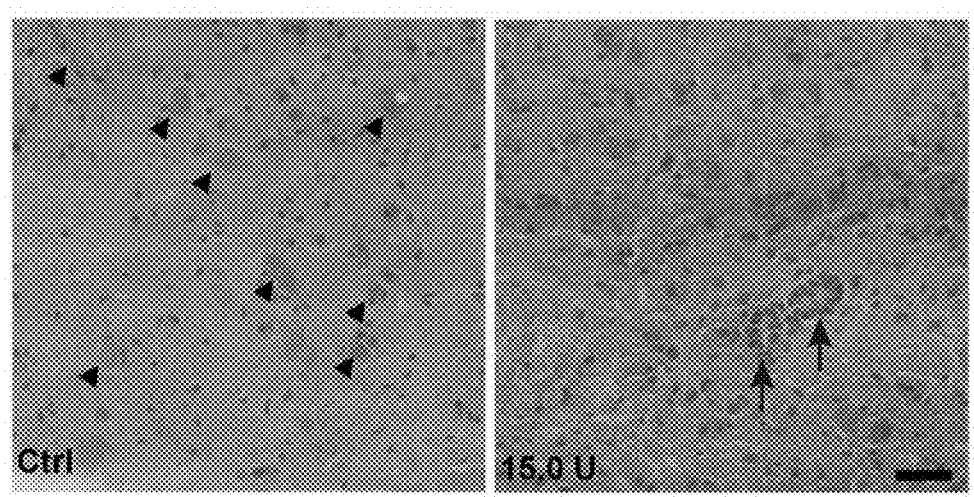
Figure 4B:
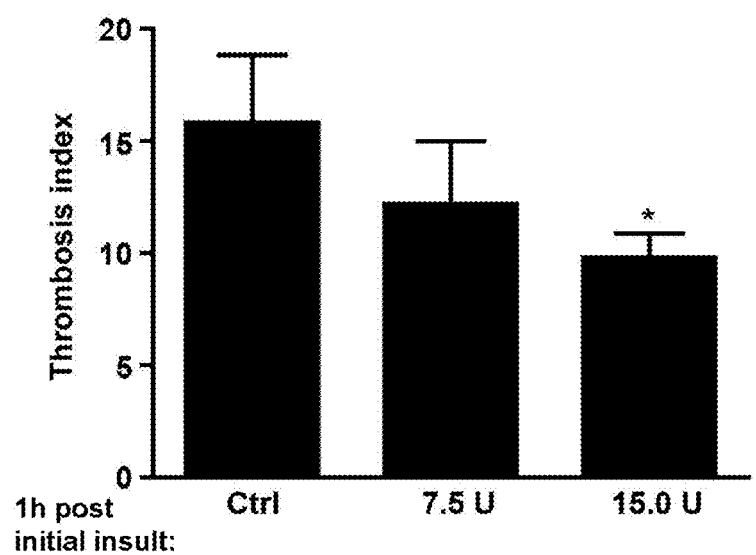
Figure 5A:
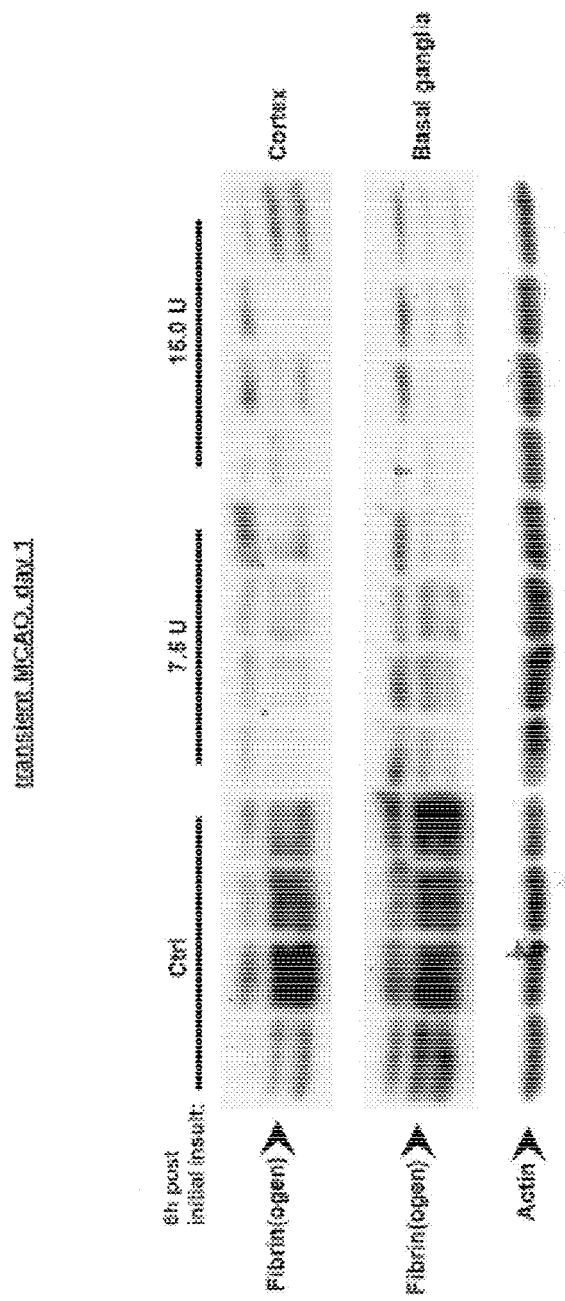
FIGS. 5A and 5B: Delayed C1-INH treatment reduces intracerebral thrombus formation. Upper panel: Accumulation of fibrin(ogen) in the infarcted cortices and basal ganglia of control mice (Ctrl) and mice treated with 7.5 U C1-INH or 15.0 U C1-INH 6h post stroke as determined by immunoblotting 24 h after tMCAO. Lower panel: Densitometric quantification of thrombus formation in the mouse groups and brain regions indicated above (n=4/group); *p<0.05, **p<0.01, ###p<0.0001, 2-way ANOVA, Bonferroni post-hoc test compared with controls (cortex (*) or basal ganglia (#), respectively).
Figure 5B:
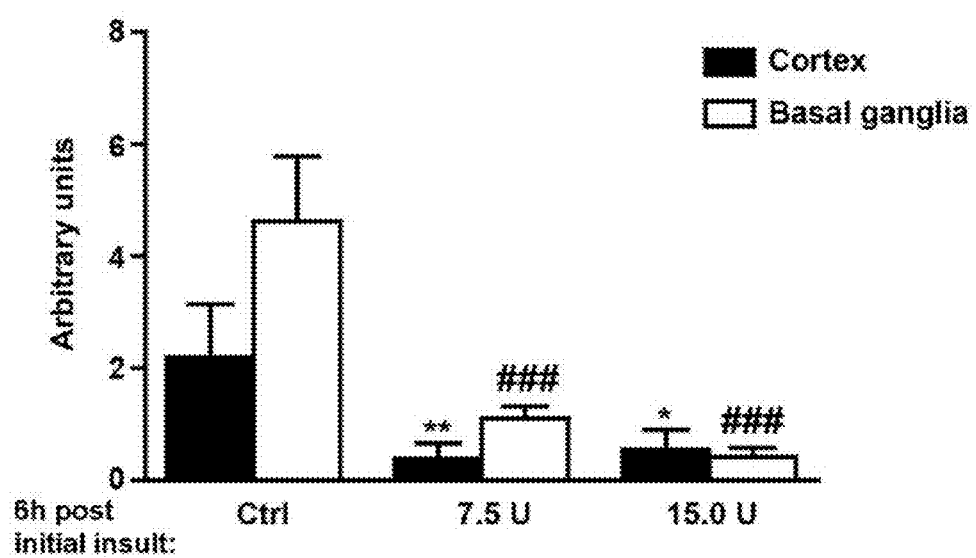

C1-INH also acts on FXIIa, the prime activator of the intrinsic pathway of blood coagulation (Alvin E. Davis III, Pedro Mejia, Fengxin Lu, *Molecular Immunology* 2008). Therefore, we analysed the impact of C1-INH on thrombotic activity after brain ischemia/reperfusion injury. Indeed, the amount of fibrin(ogen) detected by Western blot in the ischemic cortex (mean optical density $2.8\pm1.1$ [control] vs. $1.7\pm0.8$ [7.5 U] or $0.03\pm0.02$ [15.0 U], respectively; $p<0.0001$ [control vs. 15.0 U]) and basal ganglia (mean optical density $2.8\pm1.0$ [control] vs. $1.2\pm0.7$ [7.5 U] or $0.3\pm0.2$ [15.0 U], respectively; $p<0.001$ [control vs. 15.0 U]) was significantly reduced on day 1 post stroke following high-dose (15.0 U) C1-INH application 1 h after the induction of tMCAO (FIG. 4a). Accordingly, the microvascular patency was increased in C1-INH-treated mice compared with naïve controls (thrombosis index: $15.8\pm3.0$ [control] vs. $12.2\pm2.8$ [7.5 U] or $9.8\pm2.4$ [15.0 U], respectively; $p<0.05$ [control vs. 15.0 U]) (FIG. 4b). Importantly, thrombotic activity was still significantly reduced in the cortices and basal ganglia when C1-INH was applied in a delayed setting, i.e. 6 h after tMCAO (FIG. 5).

Figure 6:
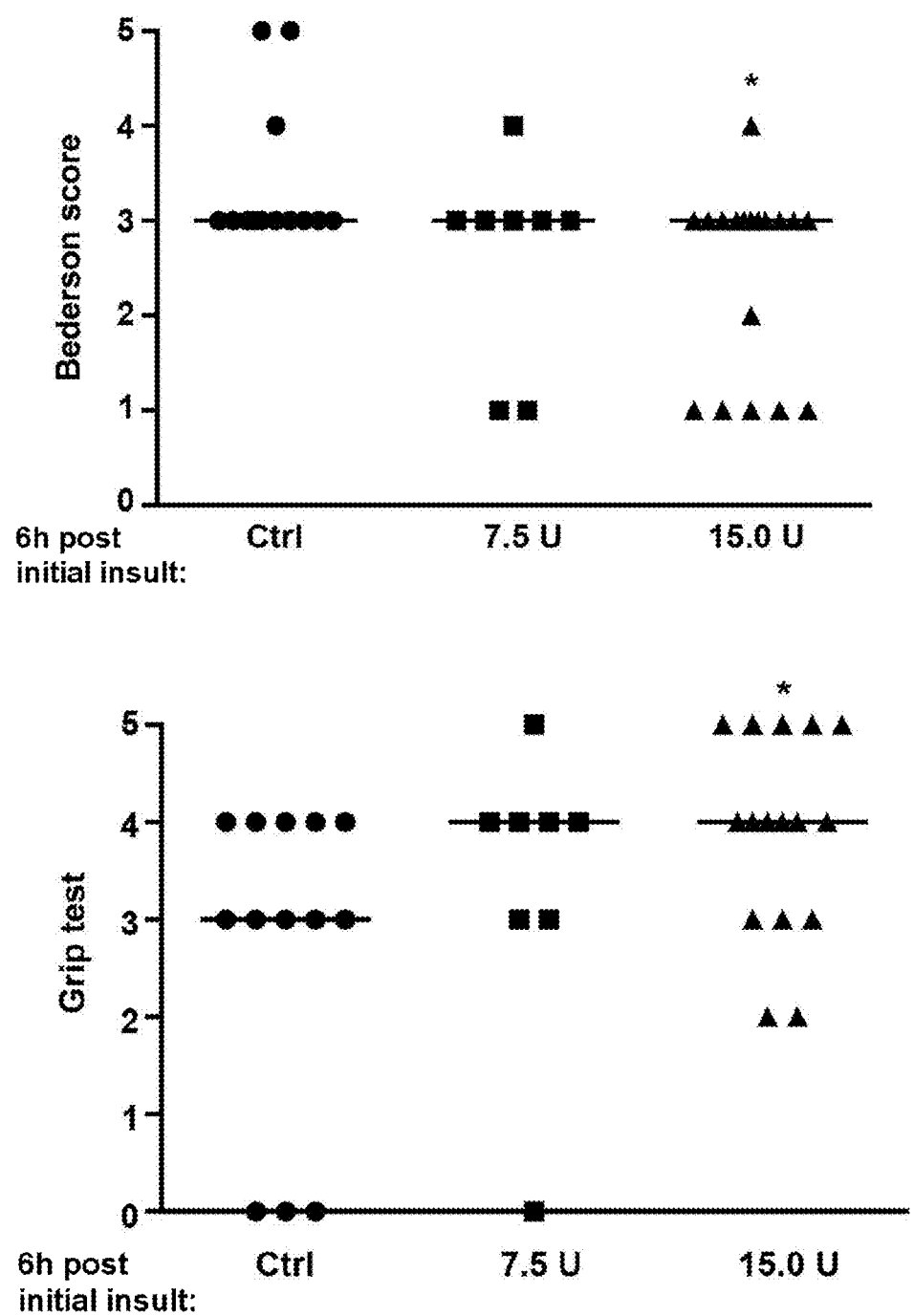
FIG. 6: C1-INH is still effective when applied in a delayed setting after tMCAO. (a) Neurological Bederson score (upper panel) and grip test score (lower panel) on day 1 after tMCAO (24 h post initial insult) in the mouse groups indicated above (n=8-16/group). Mice receiving 6 h post initial insult 15.0 U C1-INH performed significantly better compared with controls or mice receiving the lower dose (7.5 U) of C1-INH; *p<0.05, Kruskal-Wallis test followed by Dunn's multiple comparison test.

In an attempt to extend the therapeutic time window of exogenously applied C1-INH, C57Bl/6 mice also received 7.5 U or 15.0 U C1-INH in a delayed setting that is, 5 h after start of reperfusion (i.e. 6 h after the induction of tMCAO). Most notably, neurological dysfunction was still significantly less in the 15.0 U C1-INH group compared with the 7.5 U C1-INH group or control animals on day 1 (Bederson score: median 3.0 [3.0, 4.0] [control] vs. 3.0 [2.0, 3.0] [7.5 U] or 3.0 [1.0, 3.0] [15.0 U], respectively, $p<0.05$; grip test score median 3.0 [1.0, 4.0] [control] vs. 4.0 [3.0, 4.0] [7.5 U] or 4.0 [3.0, 5.0] [15.0 U], respectively, $p<0.05$) (FIG. 6).

The invention claimed is:

1. A method of preventing the formation and/or reducing the size of a secondary edema of the central nervous system (CNS) formed by an initial insult in a subject comprising:
    administering to the subject a human C1 Esterase inhibitor to prevent the formation and/or reduce the size of a secondary edema of the central nervous system (CNS) 30 minutes or more after the initial insult,
    wherein the initial insult leads to at least one disorder selected from the group consisting of stroke, ischemic stroke, hemorrhagic stroke, perinatal stroke, traumatic brain injury, and spinal cord injury,
wherein said secondary edema is substantially a vasogenic edema.

2. The method according to claim 1, wherein said secondary edema of the CNS is a secondary brain edema or a secondary spinal cord edema.

3. The method according to claim 1, wherein said secondary edema occurs 1 to 10 days after the initial insult leading to the at least one disorder selected from the group consisting of stroke, ischemic stroke, hemorrhagic stroke, perinatal stroke, traumatic brain injury, and spinal cord injury.

4. The method according to claim 3, wherein the initial injury is an occlusion of a blood vessel or a hemorrhage in the brain.

5. The method according to claim 4, wherein said subject is a human.

6. The method according to claim 1, wherein said inhibitor is a plasma-derived C1-inhibitor.

7. The method according to claim 1, wherein said inhibitor is identical with a naturally occurring human protein.

8. The method according to claim 1, wherein the size of the secondary edema is reduced by at least 10% compared to the size of the untreated secondary brain edema.

9. The method according to claim 1, wherein said inhibitor is administered intravenously or subcutaneously.

10. The method according to claim 1, wherein said inhibitor is administered in a dose of 1 to 1000 units per kg body weight.

11. The method according to claim 1, wherein said inhibitor is administered in a single dose as an injection or as an infusion.

12. The method according to claim 1, wherein said inhibitor is administered at the latest 10 days after the initial insult.

13. The method according to claim 1, wherein said inhibitor is administered at the latest 10 days after start of reperfusion following the initial insult.

14. The method according to claim 1, wherein said inhibitor is administered twice, once after the initial insult and before start of reperfusion and the second time after start of reperfusion following the initial insult.

15. The method according to claim 1, wherein said secondary edema occurs 2 to 5 days after an initial insult leading to the at least one disorder selected from the group consisting of stroke, ischemic stroke, hemorrhagic stroke, perinatal stroke, traumatic brain injury, and spinal cord injury.

16. The method according to claim 1, wherein the size of the secondary edema is reduced by at least 20% compared to the size of the untreated secondary brain edema.

17. The method according to claim 1, wherein the size of the secondary edema is reduced by at least 30% compared to the size of the untreated secondary brain edema.

18. The method according to claim 1, wherein said inhibitor is administered in a dose of 5 to 500 units per kg body weight.

19. The method according to claim 1, wherein said inhibitor is administered at the latest 5 days after the initial insult.

20. The method according to claim 1, wherein said inhibitor is administered at the latest 3 days after the initial insult.

21. The method according to claim 1, wherein said inhibitor is administered at the latest 5 days after the start of reperfusion following the initial insult.

22. The method according to claim 1, wherein said inhibitor is administered at the latest 3 days after start of reperfusion following the initial insult.

23. The method according to claim 1, wherein the C1-Inhibitor is plasma-derived Cinryze® (Viropharma), recombinant Ruconest® or Rhucin® (both Pharming), or plasma-derived Berinert® (CSL Behring).

24. A method of preventing, reducing or treating brain ischemia-reperfusion injury in a subject comprising:
administering to the subject 30 minutes or more after start of reperfusion a plasma derived human C1 Esterase inhibitor to prevent, reduce or treat brain ischemia-reperfusion injury.

25. The method according to claim 24, wherein said inhibitor is administered intravenously or subcutaneously.

26. The method according to claim 24, wherein said inhibitor is administered in a dose of 1 to 1000 units per kg body weight.

27. The method according to claim 24, wherein said inhibitor is administered between 30 minutes and 10 days after start of reperfusion.

28. The method according to claim 24, wherein said brain ischemia-reperfusion injury occurs after a disorder selected from the group consisting of stroke, ischemic stroke, hemorrhagic stroke, and perinatal stroke.

29. The method according to claim 24, wherein said inhibitor is administered in a dose of 5 to 500 units per kg body weight.

30. The method according to claim 24, wherein said inhibitor is administered between 30 minutes and 5 days after start of reperfusion.

* * * * *